(12) United States Patent
Bazin-Lee et al.

(10) Patent No.: US 11,964,014 B2
(45) Date of Patent: *Apr. 23, 2024

(54) VACCINE ADJUVANTS BASED ON TLR RECEPTOR LIGANDS

(71) Applicant: THE UNIVERSITY OF MONTANA, Missoula, MT (US)

(72) Inventors: Helene Bazin-Lee, Stevensville, MT (US); David Burkhart, Missoula, MT (US); Jay Evans, Corvallis, MT (US)

(73) Assignee: THE UNIVERSITY OF MONTANA, Missoula, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,041

(22) Filed: Aug. 8, 2023

(65) Prior Publication Data

US 2024/0024469 A1 Jan. 25, 2024

Related U.S. Application Data

(63) Continuation of application No. 17/613,414, filed as application No. PCT/US2020/034258 on May 22, 2020.

(Continued)

(51) Int. Cl.
| | | |
|---|---|---|
| *A61K 39/39* | (2006.01) | |
| *A61K 39/00* | (2006.01) | |
| *C07F 9/6561* | (2006.01) | |

(52) U.S. Cl.
CPC .......... *A61K 39/39* (2013.01); *C07F 9/65616* (2013.01); *A61K 2039/55505* (2013.01); *A61K 2039/55511* (2013.01)

(58) Field of Classification Search
CPC .......... A61K 39/39; A61K 2039/55505; A61K 2039/55511; C07F 9/65616
See application file for complete search history.

(56) References Cited

U.S. PATENT DOCUMENTS

| | | | |
|---|---|---|---|
| 4,372,945 | A | 2/1983 | Likhite |
| 4,474,757 | A | 10/1984 | Arnon et al. |

(Continued)

FOREIGN PATENT DOCUMENTS

| | | |
|---|---|---|
| CN | 102177159 A | 9/2011 |
| CN | 109310773 A | 2/2019 |

(Continued)

OTHER PUBLICATIONS

Bazin et al., "Phospholipidation of TLR7/8-active imidazoquinolines using a tandem phosphoramidite method", Tetrahedron Lett., 2016, vol. 57, pp. 2063-2066.

(Continued)

*Primary Examiner* — Adam C Milligan
*Assistant Examiner* — Amanda Michelle Petritsch
(74) *Attorney, Agent, or Firm* — Michael Best & Friedrich LLP

(57) ABSTRACT

Lipidated oxoadenines of formula (I) are TLR7/8 receptor ligands useful for modulating immune responses. The com- (Continued)

pounds may have therapeutic application in the treatment of cancer, infectious diseases, allergy, or autoimmune disorders.

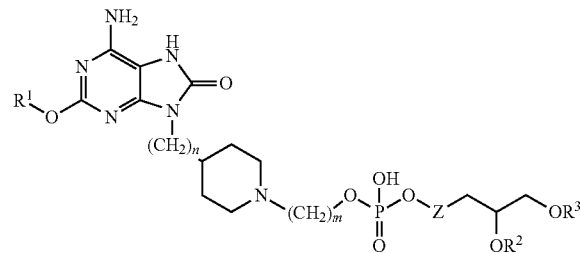

(I)

10 Claims, 8 Drawing Sheets

Related U.S. Application Data

(60) Provisional application No. 62/975,054, filed on Feb. 11, 2020, provisional application No. 62/851,941, filed on May 23, 2019.

(56) References Cited

U.S. PATENT DOCUMENTS

| | | | |
|---|---|---|---|
| 4,603,112 | A | 7/1986 | Paoletti et al. |
| 4,769,330 | A | 9/1988 | Paoletti et al. |
| 4,777,127 | A | 10/1988 | Suni et al. |
| 5,017,487 | A | 5/1991 | Stunnenberg et al. |
| 5,151,254 | A | 9/1992 | Arai et al. |
| 6,113,918 | A | 9/2000 | Johnson et al. |
| 7,063,967 | B2 | 6/2006 | Johnson et al. |
| 7,960,522 | B2 | 6/2011 | Johnson et al. |
| 8,067,413 | B2 | 11/2011 | Bonnert et al. |
| 8,624,029 | B2 | 1/2014 | Johnson |
| 8,729,088 | B2 | 5/2014 | Carson et al. |
| 9,044,481 | B2 | 6/2015 | Johnson et al. |
| 2012/0315291 | A1 | 12/2012 | Bazin-Lee et al. |
| 2013/0336996 | A1 | 12/2013 | Vernejoul et al. |
| 2018/0273560 | A1* | 9/2018 | Bazin-Lee .......... C07F 9/65616 |

FOREIGN PATENT DOCUMENTS

| | | |
|---|---|---|
| EP | 0345242 A2 | 12/1989 |
| GB | 2200651 A | 8/1988 |
| WO | 8901973 A2 | 3/1989 |
| WO | 9102805 A2 | 3/1991 |
| WO | 9420078 A1 | 9/1994 |
| WO | 9423701 A1 | 10/1994 |
| WO | 9606638 A1 | 3/1996 |
| WO | 9850399 A1 | 11/1998 |
| WO | 2010018133 A1 | 2/2010 |
| WO | 2011017611 A1 | 2/2011 |
| WO | 2017102652 A1 | 6/2017 |
| WO | 2017102654 A1 | 6/2017 |
| WO | 2017184735 A1 | 10/2017 |
| WO | 2017200852 A1 | 11/2017 |
| WO | 2017207481 A1 | 12/2017 |
| WO | 2019157509 A1 | 8/2019 |

OTHER PUBLICATIONS

Berkner, "Development of adenovirus vectors for the expression of heterologous genes", Biotechniques, vol. 6, 1988, pp. 616-627.
Chan et al., "Synthesis and characterization of PEGylated toll like receptor 7 ligands", Bioconjug. Chem., 2011, vol. 22, No. 3, pp. 445-454.
Chan et al., "Synthesis and immunological characterization of toll-like receptor 7 agonistic conjugate", Bioconjug Chem., 2009, vol. 6, pp. 1194-1200.
Chinese Patent Office Action for application 202080043550.5, dated Jul. 5, 2023 (17 pages).
Cohen, "Naked DNA Points Way to Vaccines", Science, vol. 259, 1993, pp. 1691-1692.
Coombes et al., "Single dose, polymeric, microparticle-based vaccines: the influence of formulation conditions on the magnitude and duration of the immune response to a protein antigen", Vaccine, 1996, vol. 14, No. 15, pp. 1429-1438.
Dalsgaard, "A study of the isolation and characterization of the saponin quil A", Acta Veterinia Scandinavica, 1978, vol. 69, pp. 1-40.
European Patent Office Extended European Search Report for application 20809709.7, dated Mar. 30, 2023 (7 pages).
Fischer-Hoch et al., "Protection of rhesus monkeys from fatal Lassa fever by vaccination with a recombinant vaccinia virus containing the Lass virus glycoprotein gene", Proc. Natl. Acad. Sci., vol. 86, 1989, pp. 317-321.
Flexner et al., "Attenuation and immmunogenicty in primates of vaccinia virus recombinants expressing human interleukin-2", Vaccine, vol. 8, 1990, pp. 17-21.
Guzman et al., "Efficient and Selective Adenovirus-Mediated Gene Transfer Into Vascular Neointima", Circulation, vol. 88, 1993, pp. 2838-2848.
Guzman et al., "Efficient Gene Transfer Into Myocardium by Direct Injection of Adenovirus Vectors", Cir. Res, vol. 73, 1993, pp. 1202-1207.
Hutanu et al., "Recent Application of Polyethylene Glycols (PEGs) and PEG Derivatives", Mod. Chem. Appl., 2014, vol. 2, No. 2, 6 pages.
International Preliminary Report on Patentability for Application No. PCT/US20/34258 dated dated Nov. 16, 2021 (5 pages).
International Search Report and Written Opinion for Application No. PCT/US20/34258 dated Aug. 25, 2020 (11 pages).
Kass-Eiseler et al., "Quantitative determination of adenovirus-mediated gene delivery to rat cardiac myocytes in vitro and in vivo", Proc. Natl. Acad. Scie., vol. 90, 1993, p. 11498-11502.
Khalaf et al., "Characterization of TRIF selectivity in the AGP class of lipid A mimetics: Role of secondary lipid chains", Bioorg. Med. Chem. Lett., 2015, vol. 25, No. 3, pp. 547-553.
Kolate et al., "PEG—A Versatile conjugating ligand for drugs and drug delivery systems", Journal of Controlled Release, 2014, vol. 192, pp. 67-81.
Kolls et al., "Prolonged and effective blockade of tumor necrosis factor activity through adenovirus-mediated gene transfer", Proc. Natl. Acad. Sci., vol. 91, 1994, pp. 215-219.
Mosmann et al., "TH1 and TH2 Cells: Different Patterns of Lymphokine Secretion Lead to Different Functional Properties", Ann. Rev. Immunol., vol. 7, 1989, pp. 145-173.
Moss et al., "Vaccinia Virus Expression Vectors", Ann. Rev. Immunol., vol. 5, 1987, pp. 305-324.
Paul, Fundamental Immunology, 3rd Edition. Chapter 8, Immunogenicity and Antigen Structure, 1993, pp. 243-247.
Rolland, "From Genes to Gene Medicines: Recent Advances in Nonviral Gene Delivery", Crit Rev Therap Drug Carrier Systems, vol. 15, No. 2, 1998, pp. 143-198.
Rosenfeld et al., "Adenovirus-Mediated Transfer of a Recombinant alpha1-Antitrypsin Gene to the Lung Epithelium in Vivo", Science, vol. 252, 1991, pp. 431-434.
Sela, "Antigenicity: Some Molecular Aspects", Science. vol. 166, 1969, pp. 1365-1374.
Smith et al., "Evaluation of novel synthetic TLR7/8 agonists as vaccine adjuvants," Vaccine, 2016, 34, 36: 4304-4312.
Ulmer et al., "Heterologous Protection Against Influenza by Injection of DNA Encoding a Viral Protein", Science, vol. 259, 1993, pp. 1745-1749.
Intellectual Property India Examination Report for application No. 202117055455, dated Dec. 12, 2023 (6 pages).

(56) References Cited

OTHER PUBLICATIONS

Chinese Patent Office Second Office Action for Application No. 202080043550.5, dated Jan. 17, 2024 (22 pages with translation).

* cited by examiner

VACCINE ADJUVANTS BASED ON TLR RECEPTOR LIGANDS

RELATED APPLICATIONS

This application is a continuation of U.S. patent application Ser. No. 17/613,414, filed Nov. 22, 2021, which is the U.S. national stage entry, under 35 U.S.C. § 371, of International Patent Application No. PCT/US2020/034258, filed May 22, 2020, which claims priority to U.S. Provisional Application No. 62/851,941, filed May 23, 2019, and U.S. Provisional Application No. 62/975,054, filed Feb. 11, 2020, the entire contents of which are incorporated by reference.

STATEMENT OF GOVERNMENT INTEREST

This invention was made with government support under contract number HHSN272200900036C awarded by the National Institutes of Health. The government has certain rights in the invention.

TECHNICAL FIELD

The present disclosure relates lipidated TLR7/8 receptor ligand compounds and methods of use thereof, for example as vaccine adjuvants.

BACKGROUND

The development of novel vaccine adjuvants and immunotherapies based on Toll-Like Receptor (TLR) ligands has been a rapidly expanding area of research over the past 10 years with clinical success across multiple indications and several approved products. Of the 10 known TLRs that have been identified in humans, five are associated with the recognition of bacterial components (TLRs 1, 2, 4, 5, 6) and four others (TLRs 3, 7, 8, 9) appear to be restricted to cytoplasmic compartments and are involved in the detection of viral RNA (TLRs 3, 7, 8) and unmethylated DNA (TLR9).

One of the most promising classes of immunotherapeutics includes compounds targeting TLR7/8. A few different classes of small molecules mimic the natural (U- and/or G-rich) viral ssRNA ligands of TLR7/8. These include oxoguanosines, which primarily interact with TLR7 and derivatives of adenine, which engage TLR7 and/or TLR8. One class of TLR-active adenine derivatives are the oxoadenines, which were initially developed to overcome certain side effects associated with the imidazoquinolines. Despite the fact that the oxoadenine class exhibits better overall toxicity/bioactivity profiles than imidazoquinolines, administration can still lead to a systemic inflammatory response limiting their use in human clinical settings. In fact, most of the TLR7/8 agonists currently under development tend to display toxic properties, are insoluble or unstable, and/or have insubstantial immunostimulatory effects.

There is a need, therefore, for effective and safe TLR7 and/or TLR8 receptor ligand compounds for vaccines and immunotherapeutics.

SUMMARY

In one aspect, disclosed are compounds of formula (I):

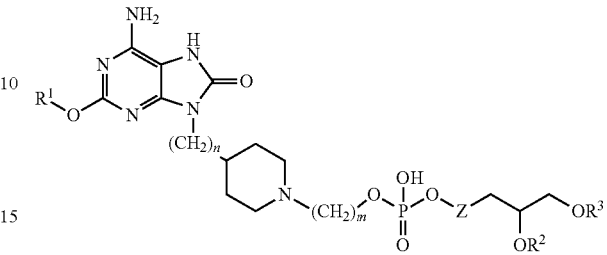

(I)

or a pharmaceutically acceptable salt thereof, wherein
$R^1$ is $C_1$-$C_8$ alkyl;
$R^2$ is H, $C_6$-$C_{20}$ alkyl, $C_6$-$C_{20}$ alkenyl, or $C(O)R^4$;
$R^3$ is $C_6$-$C_{20}$ alkyl, $C_6$-$C_{20}$ alkenyl, or $C(O)R^4$;
$R^4$, at each occurrence, is independently selected from $C_6$-$C_{20}$ alkyl and $C_6$-$C_{20}$ alkenyl;
n is 1, 2, 3, 4, 5, or 6;
m is 2, 3, 4, 5, or 6;
Z is $(C_2$-$C_6$ alkylene-O$)_q$; and
q is 1, 2, 3, 4, 5, 6, 7, 8, 9, 10, 11, 12, 13, 14, 15, 16, 17, 18, 19 or 20.

In another aspect, the invention provides a pharmaceutical composition comprising a compound of formula (I), or a pharmaceutically acceptable salt thereof, and a pharmaceutically acceptable carrier.

In another aspect, the invention provides a vaccine composition comprising a compound of formula (I), or a pharmaceutically acceptable salt thereof, and an antigen.

In another aspect, the invention provides a formulation comprising a microparticle or nanoparticle comprising a compound of formula (I), or a pharmaceutically acceptable salt thereof.

In another aspect, the invention provides an adjuvant composition comprising a compound of formula (I), or a pharmaceutically acceptable salt thereof.

In another aspect, the invention provides a method of modulating an immune response in a subject comprising administering to the subject a therapeutically effective amount of a compound of formula (I), or a pharmaceutically acceptable salt, or a pharmaceutical composition thereof.

Another aspect of the invention provides a method of treating, preventing, or reducing the susceptibility to cancer in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to an infectious disease in a subject comprising administering to a subject in need thereof a therapeutically effective amount of the compound of formula (I), or a pharmaceutically acceptable salt or a pharmaceutical composition thereof.

Another aspect of the invention provides a method of treating, preventing, or reducing the susceptibility to an allergy in a subject comprising administering to a subject in need thereof a therapeutically effective amount of the compound of formula (I), or a pharmaceutically acceptable salt or a pharmaceutical composition thereof Another aspect of the invention provides a method of treating, preventing, or reducing the susceptibility to an autoimmune condition in a subject comprising administering to a subject in need thereof a therapeutically effective amount of the compound of formula (I), or a pharmaceutically acceptable salt or a pharmaceutical composition thereof.

In another aspect, the invention provides compounds of formula (I), or a pharmaceutically acceptable salt or a pharmaceutical composition thereof, for use in a method of modulating an immune response.

In another aspect, the invention provides compounds of formula (I), or a pharmaceutically acceptable salt or a pharmaceutical composition thereof, for use in a method of treating, preventing, or reducing the susceptibility to cancer, an infectious disease, an allergy. or an autoimmune condition.

In another aspect, the invention provides the use of a compound of formula (I), or a pharmaceutically acceptable salt or a pharmaceutical composition thereof, for the manufacture of a medicament for modulating an immune response.

In another aspect, the invention provides the use of a compound of formula (I), or a pharmaceutically acceptable salt or a pharmaceutical composition thereof, for the manufacture of a medicament for treating, preventing, or reducing the susceptibility to cancer, an infectious disease, an allergy. or an autoimmune condition.

Other aspects and embodiments of the disclosure will become apparent in light of the following description and drawings.

DETAILED DESCRIPTION

Figure 1:
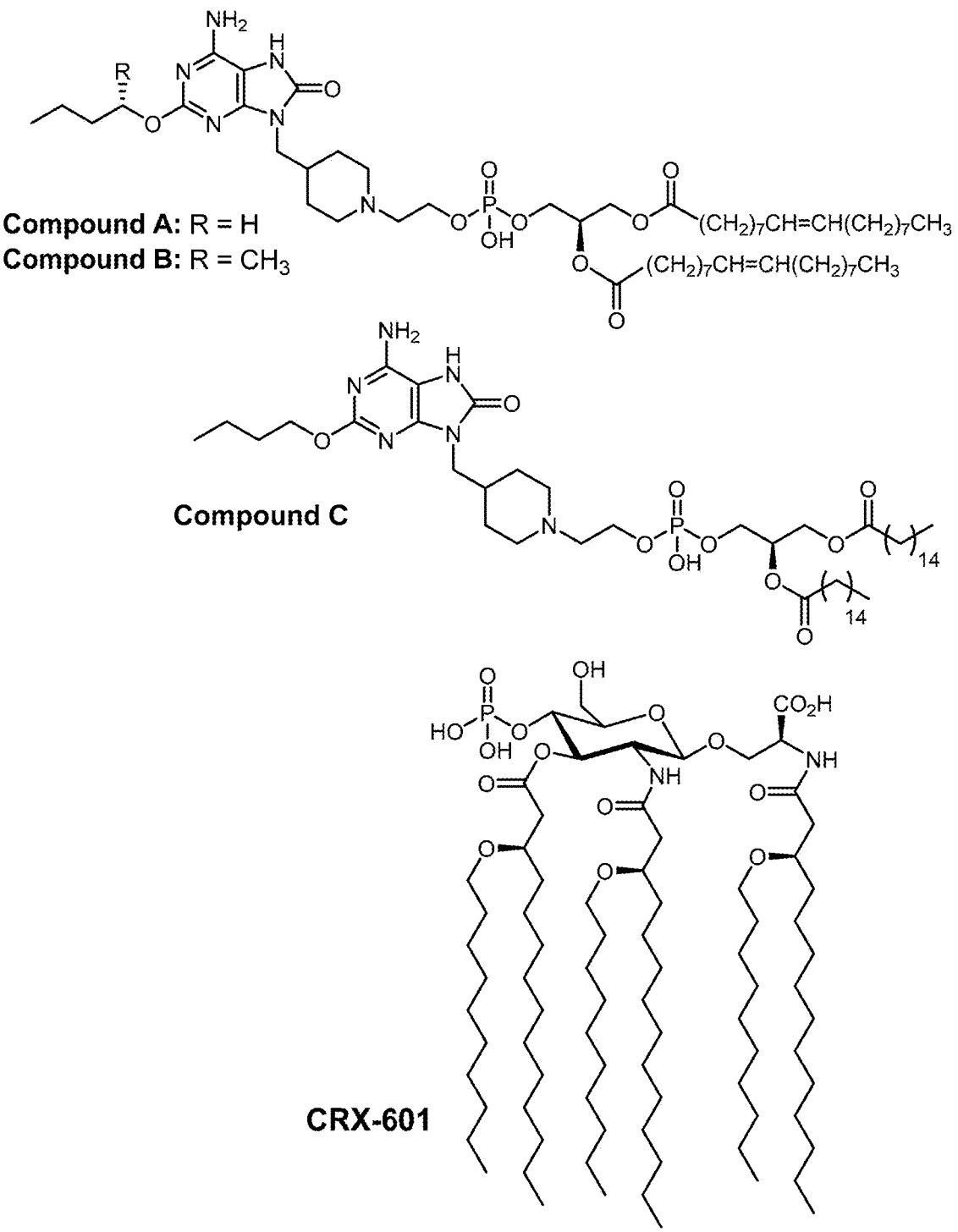
FIG. 1 shows the structural formulas of compounds CRX-601, Compound A, Compound B, and Compound C.

Described herein is a class of compounds that may act as TLR 7/8 ligands, which may be useful for novel vaccine adjuvants and immunotherapies. The TLR 7/8 ligands are novel PEGylated and lipidated oxoadenine compounds. The compounds of the invention have been shown to be inducers of interferon-α and other immunostimulatory cytokines and may possess an improved activity-toxicity profile in comparison to other known oxoadenine-based TLR 7/8 ligands.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of," and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "immune response" includes any response associated with innate and adaptive immunity including, but not limited to, increases or decreases in cytokine expression, production or secretion (e.g., IL-1, IL-6, IL-17, TNFα expression, production or secretion), cytotoxicity, immune cell migration, antibody production and/or immune cellular responses.

The phrase "modulating an immune response" or "modulation of an immune response" or "modulate an immune response" includes upregulation, potentiating, stimulating, enhancing or increasing an immune response, as defined herein.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tent-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, arylsulfonyl, aminosulfonyl, sulfinyl, —COOH, ketone, amide, carbamate, and acyl.

The term "═══" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

When substituent groups are specified by their conventional chemical formulae, written from left to right, such a formula also encompasses the same substituent that would result from writing the structure from right to left. For example, —$CH_2NH$— is also intended to encompass —$NHCH_2$—.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed is a compound of formula (I):

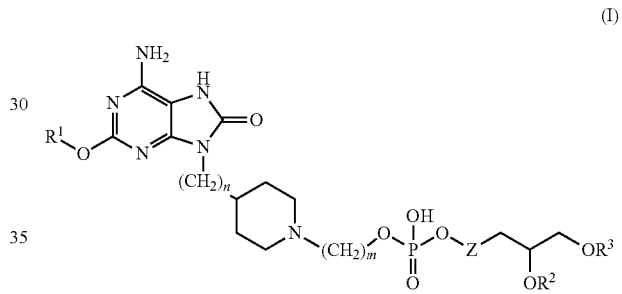

(I)

or a pharmaceutically acceptable salt thereof, wherein
$R^1$ is $C_1$-$C_8$ alkyl;
$R^2$ is H, $C_6$-$C_{20}$ alkyl, $C_6$-$C_{20}$ alkenyl, or $C(O)R^4$;
$R^3$ is $C_6$-$C_{20}$ alkyl, $C_6$-$C_{20}$ alkenyl, or $C(O)R^4$;
$R^4$, at each occurrence, is independently selected from $C_6$-$C_{20}$ alkyl and $C_6$-$C_{20}$ alkenyl;
n is 1, 2, 3, 4, 5, or 6;
m is 2, 3, 4, 5, or 6;
Z is $(C_2$-$C_6$ alkylene-O$)_q$; and
q is 1, 2, 3, 4, 5, 6, 7, 8, 9, 10, 11, 12, 13, 14, 15, 16, 17, 18, 19 or 20.

In some embodiments, $R^2$ is hydrogen or $C(O)R^4$, wherein $R^4$, when present, is independently selected from $(CH_2)_{10}CH_3$, $(CH_2)_{12}CH_3$, $(CH_2)_{14}CH_3$, $(CH_2)_{16}CH_3$, and $(CH_2)_7CH$═$CH(CH_2)_7CH_3$ at each occurrence.

In some embodiments, $R^3$ is $C(O)R^4$, wherein $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH$═$CH(CH_2)_7CH_3$.

In some embodiments, $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH$═$CH(CH_2)_7CH_3$. In some embodiments $R^4$ is $(CH_2)_{14}CH_3$.

In some embodiments, $R^2$ and $R^3$ are each $C(O)R^4$, wherein $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH$═$CH(CH_2)_7CH_3$. In some embodiments, $R^2$ and $R^3$ are each $C(O)R^4$, wherein $R^4$, at each occurrence, is $(CH_2)_{14}CH_3$.

In some embodiments, $R^2$ is hydrogen and $R^3$ is $C(O)R^4$, wherein $R^4$ is selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$.

In some embodiments, n is 1. In some embodiments, m is 2. In exemplary embodiments, n is 1 and m is 2.

In some embodiments, Z is $(C_2$ alkylene-O$)_q$, wherein q is 3, 6, 9, 12, or 16. In exemplary embodiments, q is 3. q may be 3, 6, 9, 12, or 16 in any of the embodiments herein.

The alkylene of Z may be a straight chain alkylene, i.e., n-alkylene. For example, Z may be $(C_2$-$C_6$ n-alkylene-O$)_q$. Z may be $(CH_2CH_2\text{—}O)_q$. Z may be $(CH_2CH_2\text{—}O)_3$. Z may be $(CH_2CH_2\text{—}O)_6$, Z may be $(CH_2CH_2\text{—}O)_9$, Z may be $(CH_2CH_2\text{—}O)_{12}$, or Z may be $(CH_2CH_2\text{—}O)_{16}$.

In the compounds disclosed herein, Z is oriented with the terminal carbon of Z attached to the phosphate moiety and the oxygen of Z being part of the glycerol moiety, as shown in formula (II).

$R^4$, at each occurrence, is independently selected from $C_6$-$C_{20}$ alkyl and $C_6$-$C_{20}$ alkenyl;

n is 1, 2, 3, 4, 5, or 6;

m is 2, 3, 4, 5, or 6;

Z is $(C_2$-$C_6$ alkylene-O$)_q$; and q is 1, 2, 3, 4, 5, 6, 7, 8, 9, 10, 11, 12, 13, 14, 15, 16, 17, 18, 19 or 20.

In some embodiments, $R^2$ is hydrogen or $C(O)R^4$, wherein $R^4$, when present, is independently selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$ at each occurrence.

In some embodiments, $R^3$ is $C(O)R^4$, wherein $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$.

In some embodiments, $R^4$, at each occurrence, is independently selected from $(CH_2)_{10}CH_3$, $(CH_2)_{12}CH_3$,

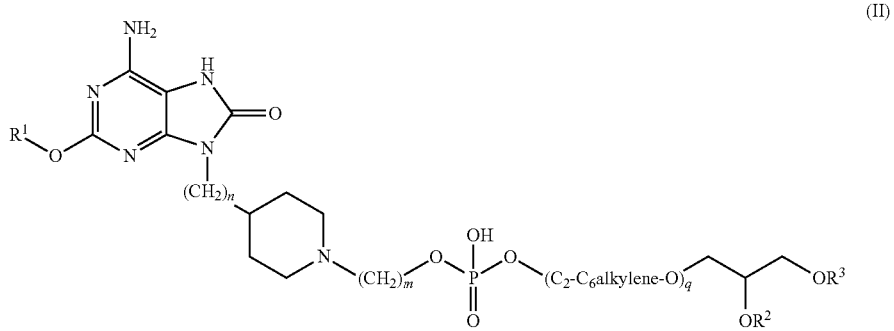

(II)

In another aspect, disclosed is a compound of formula (Ia):

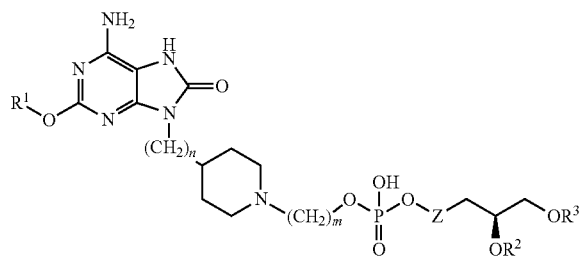

(Ia)

or a pharmaceutically acceptable salt thereof, wherein $R^1$ is $C_1$-$C_8$ alkyl;

$R^2$ is H, $C_6$-$C_{20}$ alkyl, $C_6$-$C_{20}$ alkenyl, or $C(O)R^4$;

$R^3$ is $C_6$-$C_{20}$ alkyl, $C_6$-$C_{20}$ alkenyl, or $C(O)R^4$;

$(CH_2)_{14}CH_3$, $(CH_2)_{16}CH_3$, and $(CH_2)_7CH=CH(CH_2)_7CH_3$. In some embodiments $R^4$ is $(CH_2)_{14}CH_3$.

In some embodiments, $R^2$ and $R^3$ are each $C(O)R^4$, wherein $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$. In some embodiments, $R^2$ and $R^3$ are each $C(O)R^4$, wherein $R^4$, at each occurrence, is $(CH_2)_{14}CH_3$.

In some embodiments, $R^2$ is hydrogen and $R^3$ is $C(O)R^4$, wherein $R^4$ is selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$.

In some embodiments, n is 1. In some embodiments, m is 2. In exemplary embodiments, n is 1 and m is 2.

In some embodiments, Z is $(C_2$ alkylene-O$)_q$, wherein q is 3, 6, 9, 12, or 16. In exemplary embodiments, q is 3.

The compound, or a pharmaceutically acceptable salt thereof, selected from the group consisting of:

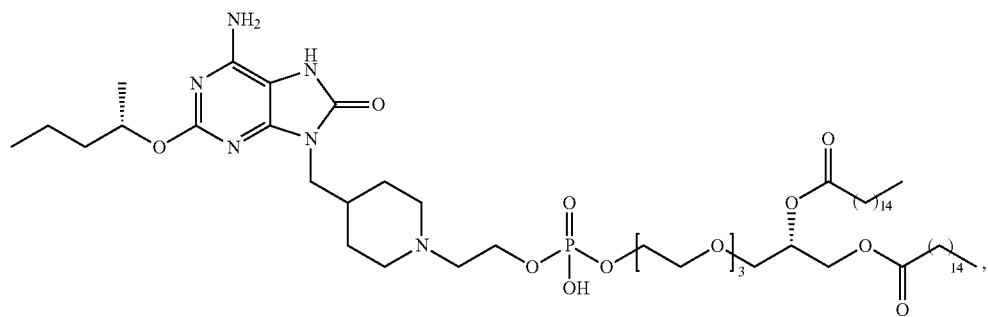
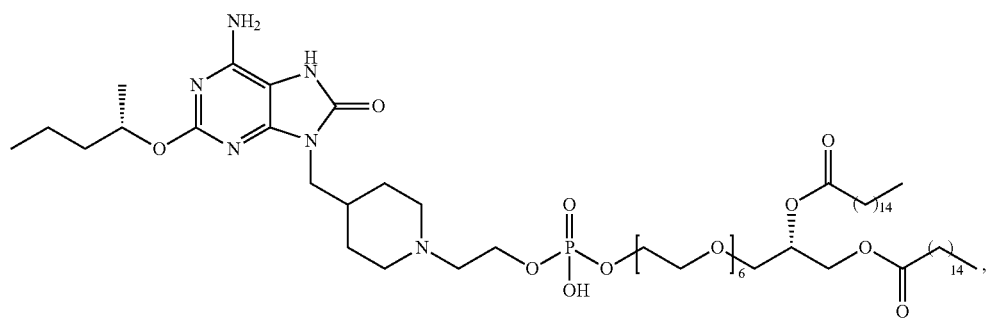
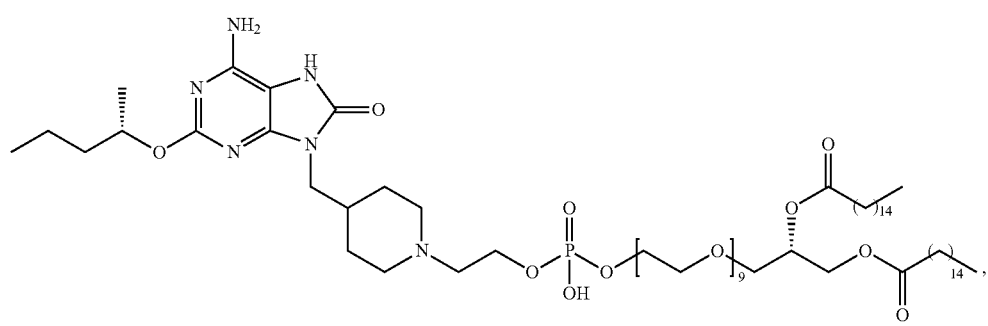
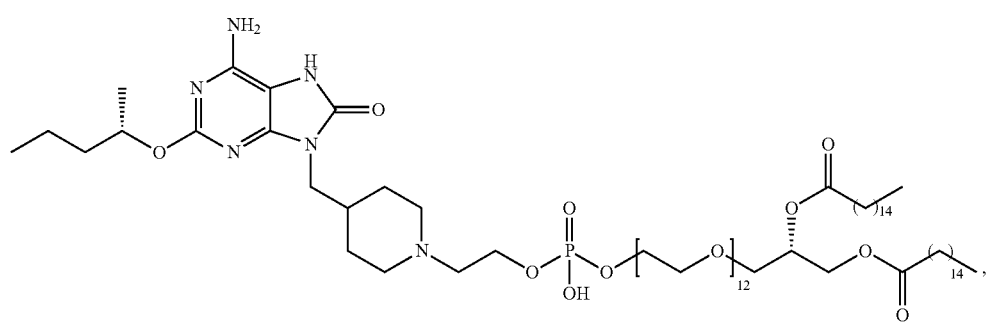
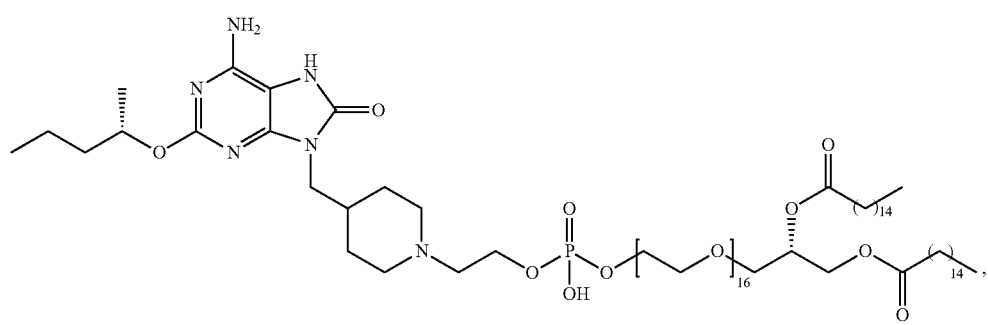

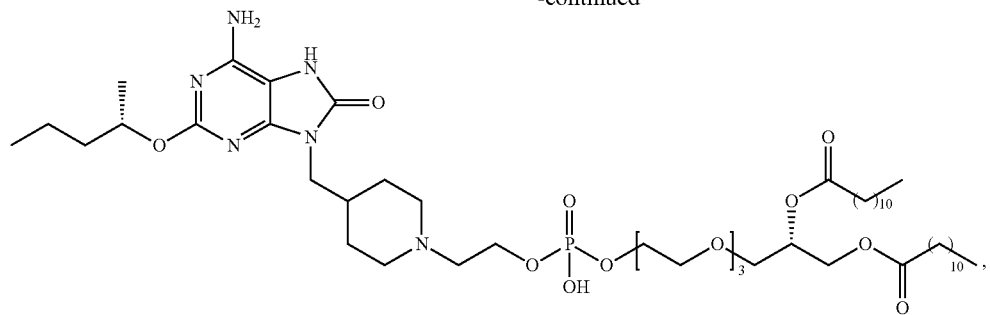

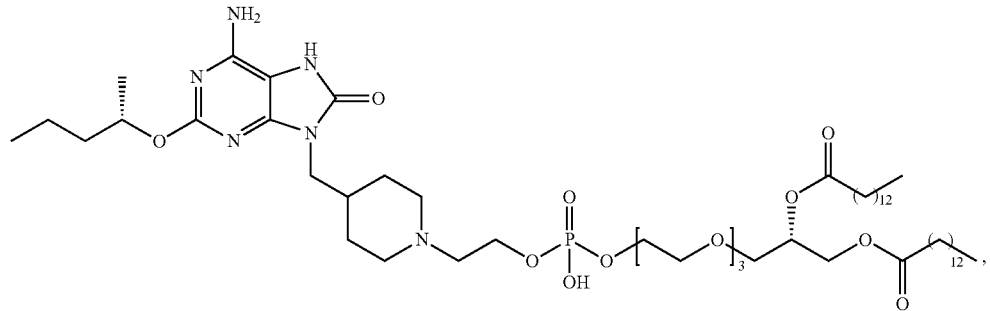

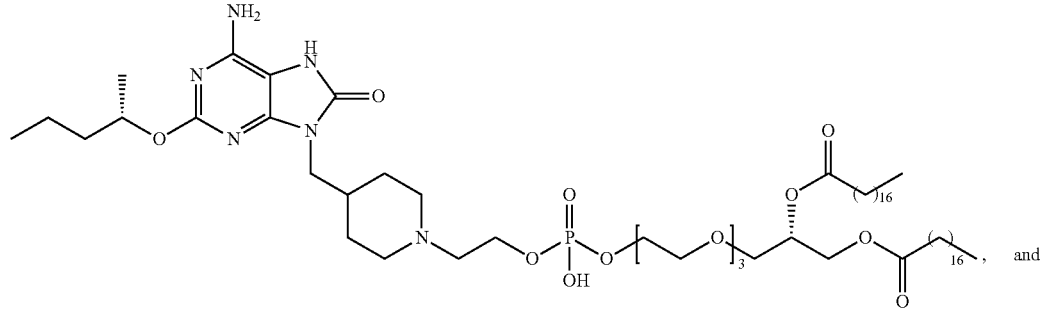

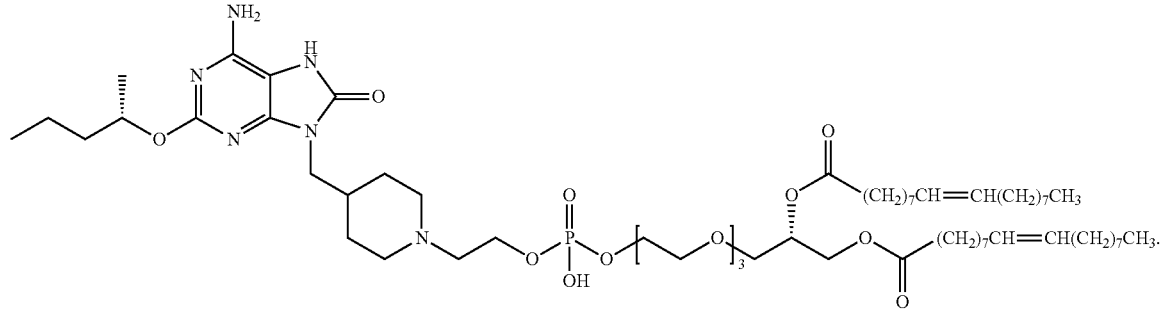

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in *Pure Appl. Chem.*, 1976, 45: 13-30. The disclosure contemplates various stereoisomers and mixtures thereof and these are specifically included within the scope of this disclosure. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England (or more recent versions thereof), or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group or phosphate group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like. In some embodiments, the pharmaceutically acceptable salt is a choline salt.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

The compounds described herein, or the pharmaceutically acceptable salts thereof, may be included in a formulation. The formulation may comprise a microparticle or a nanoparticle that includes, but is not limited to, a liposome, a micelle, a polymer, a block co-polymer, silica, an emulsion, or a combination thereof. The formulation may comprise organic, inorganic, and/or lipid constituents, and may contribute to the immunomodulatory effect of the compound and/or may impact the biodistribution, bioavailability and/or the toxicity characteristics of the compound.

b. Biological Activity

The compounds disclosed herein, including compounds of formula (I) may have biological activity that makes them useful as immunologic adjuvants or immunomodulators. For example, the compounds may stimulate the immune system's response to a co-administered antigen. In some embodiments, the compounds of formula (I) are TLR7 antagonists. In some embodiments, the compounds formula (I) are TLR8 antagonists. In some embodiments, the compounds have activity as Th1 stimulating adjuvants.

In some embodiments, the compounds may simulate the production of cytokines in a sample or when administered to a subject. The compounds may stimulate the production of Th1-type cytokines. Exemplary cytokines include IFN-γ, IL-2 and IL-12. Such activity may be tested according to established methods. For example, the levels of such cytokines may be measured in samples of peripheral blood mononuclear cells (PBMCs) after exposure to the compounds.

Conditions which may be mediated by TLR7 and/or TLR8 activity include but are not limited to, inflammation, including but not limited to inflammatory or allergic diseases such as asthma, allergic rhinitis, hypersensitivity lung diseases, eosinophilic pneumonitis, delayed-type hypersensitivity, atherosclerosis, pancreatitis, gastritis, osteoarthritis, psoriasis, sarcoidosis, pulmonary fibrosis, respiratory distress syndrome, bronchiolitis, chronic obstructive pulmonary disease, sinusitis, cystic fibrosis, and dermatitis; autoimmune diseases including but not limited to rheumatoid arthritis, psoriatic arthritis, systemic lupus erythematosus, Sjogrens disease, ankylosing spondylitis, scleroderma, diabetes, graft rejection, including graft-versus-host disease, inflammatory bowel diseases including, but not limited to, Crohn's disease and ulcerative colitis; infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumo virus, parainfluenza virus, SARS), and West Nile virus; microbial infections caused by, for example, bacteria, fungi, or protozoa including, but not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis; various cancers, in particular the treatment of cancers that are known to be responsive to immunotherapy and including, but not limited to, renal cell carcinoma, lung cancer, breast cancer, colorectal cancer, bladder cancer, melanoma, leukemia, lymphomas and ovarian cancer; basal cell carcinoma; actinic keratosis; genital papilloma viral infections; and liver regeneration. various cancers, in particular the treatment of cancers that are known to be responsive to immunotherapy and including, but not limited to, renal cell carcinoma, lung cancer, breast cancer, colorectal cancer, bladder cancer, melanoma, leukemia, lymphomas and ovarian cancer; basal cell carcinoma; actinic keratosis; genital papilloma viral infections; and liver regeneration.

3. COMPOSITIONS

The disclosed compounds may be incorporated into pharmaceutical compositions, adjuvant compositions, and vaccine compositions that may be suitable for administration to a subject (such as a patient, which may be a human or non-human).

a. Pharmaceutical Compositions

The disclosed compounds may be incorporated into pharmaceutical compositions. The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The pharmaceutical compositions and formulations may include additional therapeutic agents. In some embodiments, the additional therapeutic agent is an adjuvant, an immunostimulant, a chemotherapeutic agent, an immune modulatory agent or a combination thereof.

The pharmaceutical compositions and formulations may include an adjuvant. Adjuvants are additives that enhance humoral and/or cell mediated immune responses to a vaccine antigen. Any adjuvant may be useful in the pharmaceutical compositions and formulations described herein. The adjuvant may interact with a member of members of the TLR family. In some embodiments, the adjuvant is a TLR4 ligand.

TLR4 ligands include CRX-601 (FIG. 1), monophosphoryl lipid A (MPLA), glucopyranosyl lipid A (GLA), CRX-547

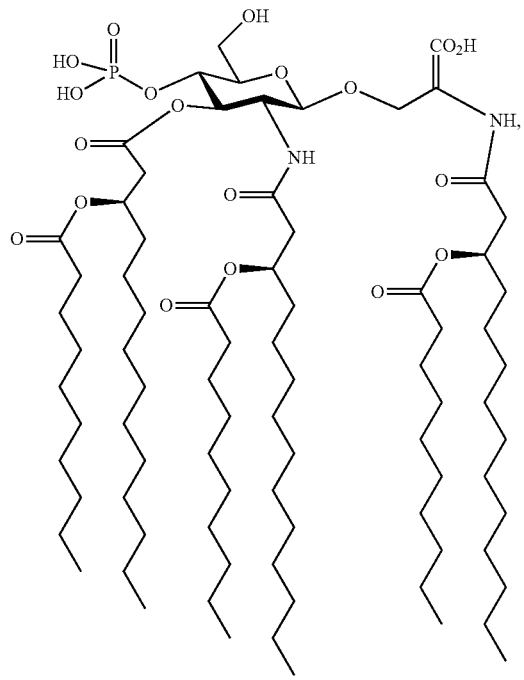

aminoalkyl glucosamide 4-phosphate (AGP) class lipid A mimetics, and other TLR4 ligands described in Khalaf et al., Bioorg. Med. Chem. Lett. (2015) 25(3), 547-553, and U.S. Pat. Nos. 7,960,522 and 7,063,967, which are incorporated herein by reference. Other TLR4 ligands include compounds described in WO2019/157509, which is incorporated herein by reference. For example, the TLR4 ligand may be

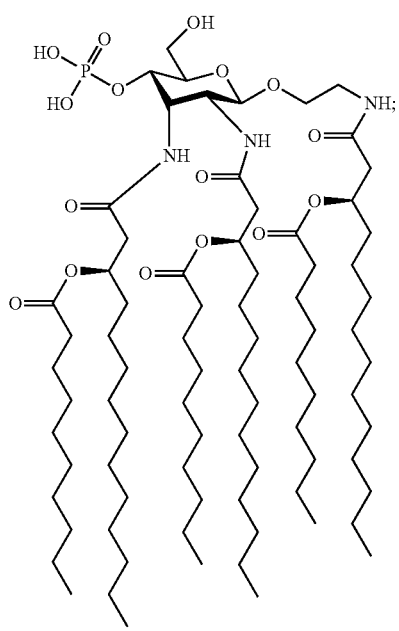

17
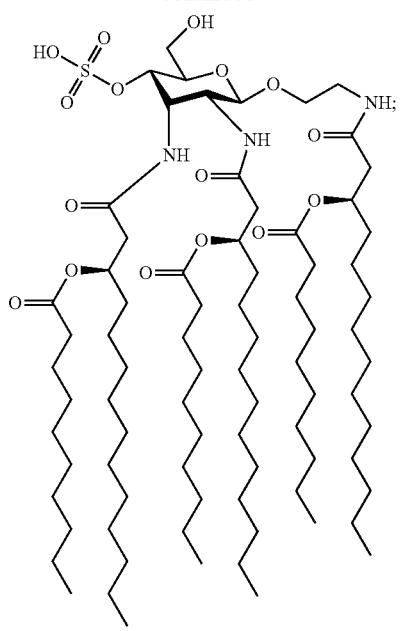
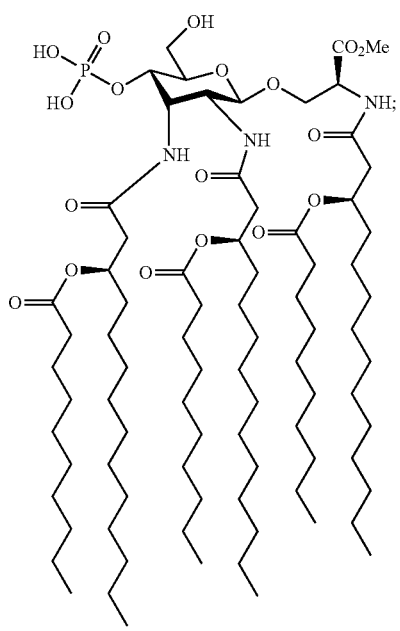
18
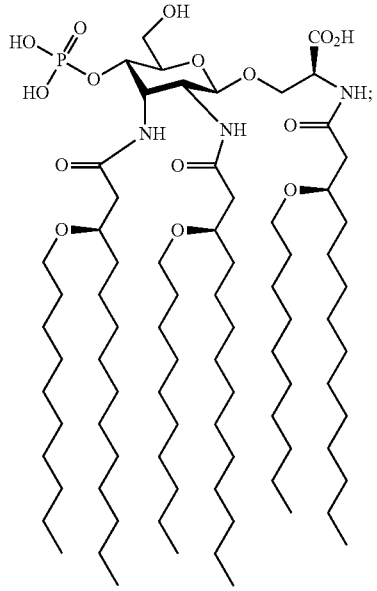
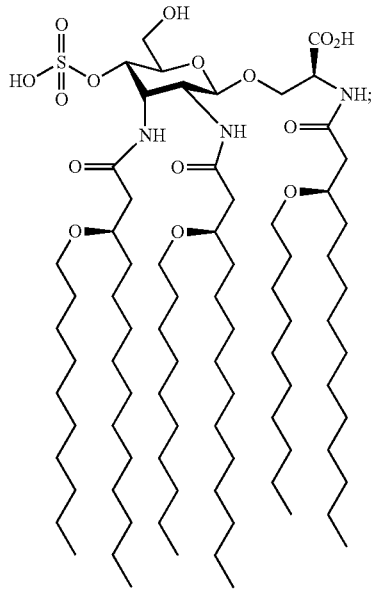

19
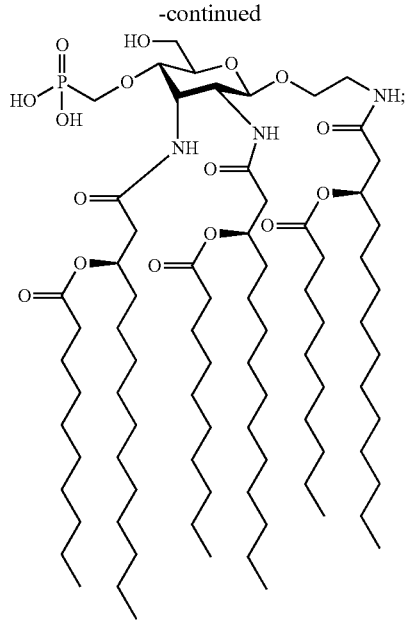
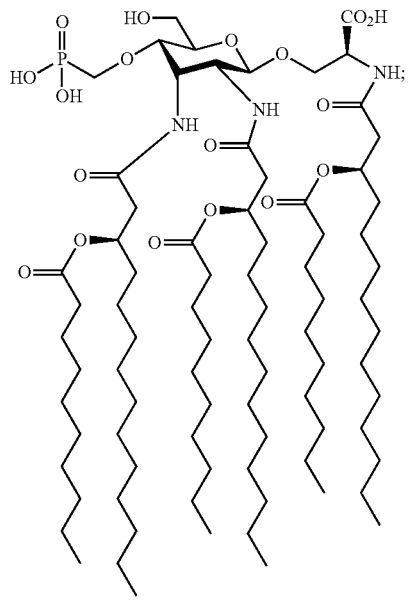
20
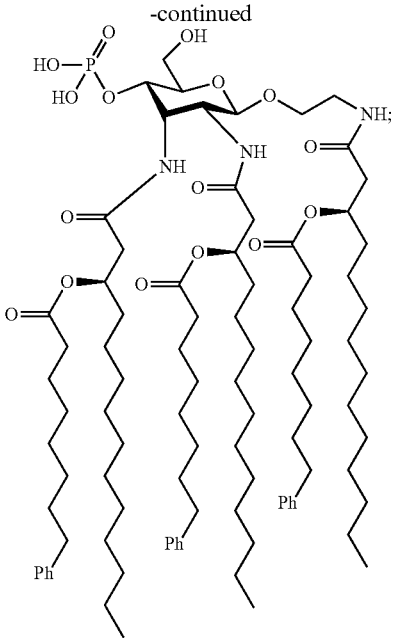
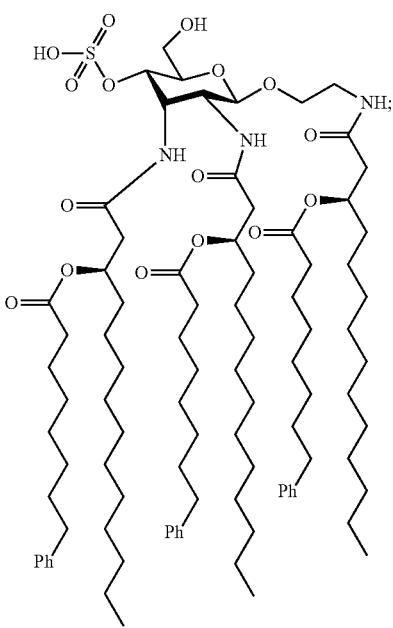

21
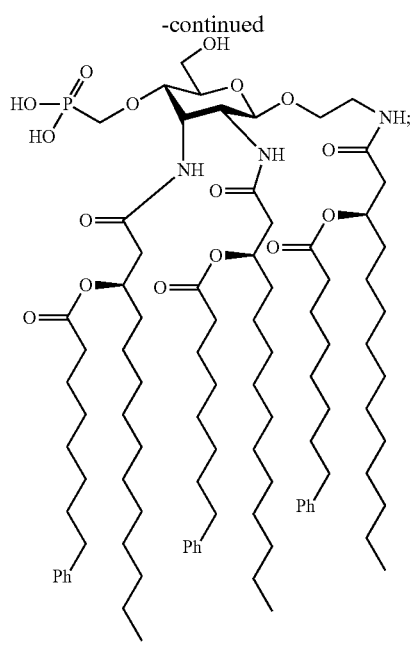
22
-continued
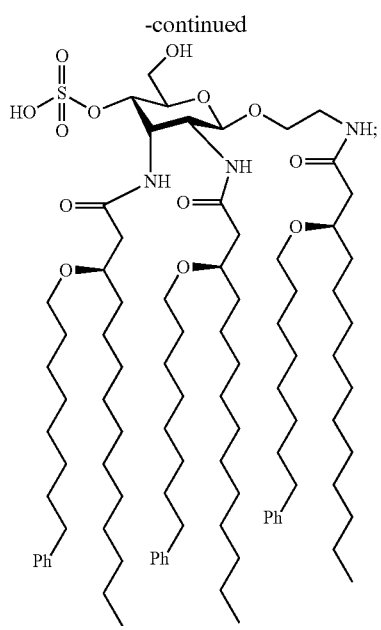
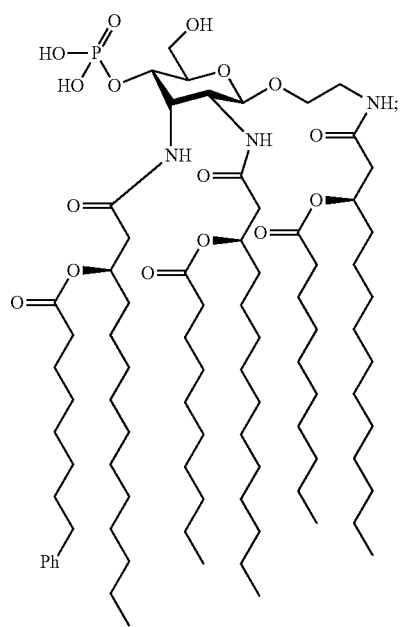
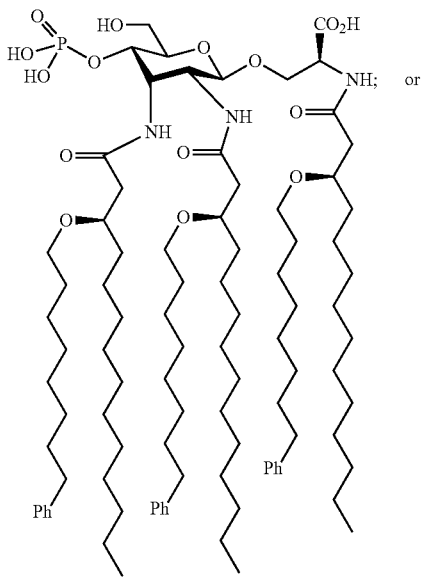
; or

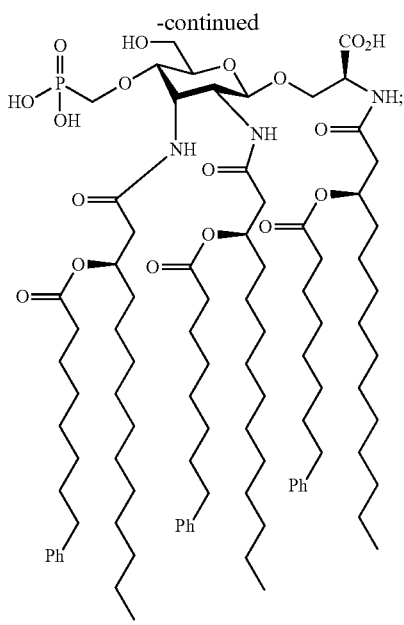

or a pharmaceutically acceptable salt thereof.

In some embodiments, the adjuvant is an aluminum salt. The aluminum salt may include phosphate, sulfate, hydroxide, or a combination thereof. In some embodiments, the aluminum salt is potassium aluminum sulphate, which may be in hydrated form. The alumimun salt may also be an aluminum hydroxide gel. The alumimun salt may also be an aluminium phosphate wet gel. Aluminum salt adjuvants may be referred to as alum. In some embodiments, a compound as disclosed herein is adsorbed to the aluminum salt.

The pharmaceutical composition may further comprise an antigen. In some embodiments, the antigen is adsorbed to the aluminum salt with a compound disclosed herein. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed. In some embodiments, the antigen is derived from a bacterium, virus, bacteriophage, fungus, prion, neoplasm, autoantigen, animal, plant, recombinant or synthetic material. In one embodiment, the antigen in a vaccine composition is in the form of a peptide, polypeptide, a protein, or immunogenic portion thereof. In some embodiments, the antigen is a hapten, a hapten conjugated to a carrier protein, polypeptide or other polymer, or derivatives thereof. In some embodiments the antigen is an allergen.

The pharmaceutical compositions and formulations may include an immunostimulant. Immunostimulants stimulate the immune system by inducing activation or increasing activity of any of its components. Any of the many known molecules or compounds with immunostimulant activity can be used in the disclosed pharmaceutical compositions and formulations.

The pharmaceutical compositions and formulations may include a chemotherapeutic agent. The chemotherapeutic may include any drug used in cancer treatment or any radiation sensitizing agent. Chemotherapeutics may include alkylating agents (including, but not limited to, cyclophosphamide, mechlorethamine, chlorambucil, melphalan, dacarbazine, nitrosoureas, and temozolomide), anthracyclines (including, but not limited to, daunorubicin, doxorubicin, epirubicin, idarubicin, mitoxantrone, and valrubicin), cytoskeletal disruptors or taxanes (including, but not limited to, paclitaxel, docetaxel, abraxane, and taxotere), epothilones, histone deacetylase inhibitors (including, but not limited to, vorinostat and romidepsin), topoisomerase inhibitors (including, but not limited to, irinotecan, topotecan, etoposide, tenoposide, and tafluposide), kinase inhibitors (including, but not limited to, bortezomib, erlotinib, gefitinib, imantinib, vemurafenib, and vismodegib), nucleotide analogs and precursor analogs (including, but not limited to, azacitidine, azathioprine, capecitabine, cytarabine, doxifluridine, fluorouracil, gemcitabine, hydroxyurea, mercaptopurine, methotrexate, and tioguanine), peptide antibiotics (including, but not limited to, bleomycin and actinomycin), platinum-based agents (including, but not limited to, carboplatin, cisplatin and oxaliplatin), retinoids (including, but not limited to, tretinoin, alitretinoin, and bexarotene), vinca alkaloids and derivatives (including, but not limited to, vinblastine, vincristine, vindesine, and vinorelbine), or combinations thereof.

The pharmaceutical compositions and formulations may include an immune modulatory agent. Immune modulatory agents include interferons, antigens, tumor phagocytosis-inducing agents, and other immune-enhancing agents (e.g., immune checkpoint inhibitors). The immune modulatory agent may be an immune checkpoint inhibitor, a tumor phagocytosis-inducing agent, or a combination thereof.

Interferons include interferon alpha, interferon alpha-2a, interferon alpha-2b, interferon beta, interferon gamma-1a, ACTIMMUNE® (interferon gamma-1b), or interferon gamma-n1, combinations thereof and the like.

In some embodiments the immune modulatory agent is an immune checkpoint inhibitor. Immune checkpoints regulate T cell function in the immune system. T cells play a central role in cell-mediated immunity. Checkpoint proteins interact with specific ligands which send a signal into the T cell and essentially switch off or inhibit T cell function. Checkpoint inhibitor therapies, which 'unblock' an existing immune response or which unblock the initiation of an immune response. Since many of the immune checkpoints are regulated by interactions between specific receptor and ligand pairs, monoclonal antibodies or other agents can be used to block this interaction and prevent immunosuppression. The checkpoint inhibitor may be a biologic therapeutic, a small molecule, a monoclonal antibody, a humanized antibody, a fully human antibody, a fusion protein or a combination thereof. The checkpoint inhibitor may inhibit a checkpoint protein, including, for example CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands. The checkpoint inhibitor may interact with a ligand of a checkpoint protein, including, for example CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and the B-7 family ligands.

Immune checkpoint inhibitors include PD-1 inhibitors (e.g. nivolumab, pidilizumab, sintilimab), PD-L1 inhibitors (e.g. atezolizumab, avelumab, durvalumab, BMS-936559), CTLA4 inhibitors (e.g. ipilimumab, tremelimumab) or IDO inhibitors (e.g. indoximod, epacadostat).

In some embodiments, the immune modulatory agent is a tumor phagocytosis-inducing agent. Immunostimulatory cell surface polypeptides and their receptors are important for the clearance and destruction of foreign materials, including mammalian cells or bacteria. Immunostimulatory cell surface polypeptides and their receptors activate the phagocytosis. A phagocytosis-inducing agent may induce cell surface polypeptides and their receptors to activate phagocytosis. Tumor phagocytosis-inducing agents include anti-CD47 monoclonal antibodies (e.g., Hu5F9-G4, CC-90002, ZF1, AMMS4-G4, IBI188, SRF231), anti-SIRPα fusion proteins (e.g., TTI-621, TTI-622), anti-SIRPα monoclonal antibodies (e.g., OSE-172), anti-CD47/antitumor-associated antigen bispecific antibodies, and inhibitors of leukocyte immunoglobulin-like receptor B1 (LILRB1) binding to major histocompatibility complex class 1 β2-microglobulin (MHC class1 β2M). Anti-CD47/antitumor-associated antigen bispecific antibodies include anti-CD47/CD19 bispecific antibodies (e.g., TG-1801), anti-CD47/mesothelin bispecific antibodies (e.g., NI-1801), anti-CD47/4-1BB bispecific antibodies (e.g., DSP107), anti-CD47/CD20 bispecific antibodies, anti-CD47/CD33 bispecific antibodies (e.g., HMBD004).

Other immune modulating agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE®(lenograstim), lentinan, leukocyte alpha interferon, imiquimod, MDX-010, melanomavaccine, mitumomab, molgramostim, MYLOTARGTM® (gemtuzumab ozogamicin), NEUPOGEN® (filgrastlm), OncoVAC-CL, OvaRex® (oregovomab), pemtumomab(Y-muHMFG1), PROVENGE®, sargaramostim, sizofilan, teceleukin, TheraCys®, ubenimex, VIRULIZIN®, Z-1OO, WF-1O, PROLEUKIN® (aldesleukin), ZADAXIN® (thymalfasin), ZENAPAX® (daclizumab), ZEVALIN® (90Y-Ibritumomab tiuxetan) and the like including but not limited to STING (stimulator of interferon genes) and NOD (nucleotide-binding oligomerization domain-like receptors) Agonists.

In the methods and uses described herein, the pharmaceutical combination of the compound of formula (I), or a pharmaceutically acceptable salt, or composition thereof; and an adjuvant and/or immunomodulatory agent may be administered/used simultaneously, separately, or sequentially, and in any order, and the components may be administered separately or as a fixed combination. For example, therapeutic treatment according to the invention may comprise administration of a first active ingredient in free or pharmaceutically acceptable salt form and administration of a second active ingredient in free or pharmaceutically acceptable salt form, simultaneously or sequentially in any order, in jointly therapeutically effective amounts or effective amounts, e.g. in daily dosages corresponding to the amounts described herein. The individual active ingredients of the combination can be administered separately at different times during the course of therapy or concurrently in divided or single dosage forms. The instant invention is therefore to be understood as embracing all such regimes of simultaneous or alternating treatment and the term "administering" is to be interpreted accordingly. Thus, a pharmaceutical combination, as used herein, defines either a fixed combination in one dosage unit form or separate dosages forms for the combined administration where the combined administration may be independently at the same time or at different times. As a further example, adjuvants or immunomodulatory agents may be administered/used simultaneously (e.g., through coinjection), separately, or sequentially, followed by administration of the compound of formula (I), or vice versa.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, sublingual, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, polyols (such as glycerol, propylene glycol, polyethylene glycol and the like), and phosphate buffer solutions. The amount of solvent(s) in a systemic or topical composition is typically from about 0 to about 100%. In one embodiment compounds of the invention are formulated in 2% glycerol in sterile water. In a further embodiment, the compound UM-1007 is formulated in 2% glycerol in sterile water. The 2% glycerol in sterile water formulations may be for parenteral administration.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp.587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

b. Adjuvant and Vaccine Compositions

The compounds may also be incorporated into adjuvant compositions and vaccine compositions. The adjuvant composition may induce an immune response. In some embodiments, the adjuvant composition induces a Th1 type immune response.

The vaccine compositions may further include an antigen. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed. In some embodiments, the antigen is derived from a bacterium, virus, bacteriophage, fungus, prion, neoplasm, autoantigen, animal, plant, recombinant or synthetic material. Antigens include bacterial, viral, fungal, plant, and cancer/tumor antigens described in WO2019/157509, which is incorporated herein by reference.

The adjuvant and vaccine compositions may include an "effective amount" of the disclosed compound. In the context of an adjuvant or vaccine composition, an "effective amount" refers to an amount effective, at dosages and for periods of time necessary, to achieve the desired result (e.g., to potentiate an immune response to one or more antigens). The immune response can be measured, for example, by measuring antibody titers against an antigen, assessing the ability of a vaccine containing the compound to immunize a host in response to a disease or antigen challenge, etc. For example, administering an "effective amount" of a compound or composition to a subject increases one or more antibody titers by 10% or more over a nonimmune control, by 20% or more over a nonimmune control, by 30% or more over a nonimmune control, by 40% or more over a nonimmune control, by 50% or more over a nonimmune control, by 50% or more over a nonimmune control, by 70% or more over a nonimmune control, by 80% or more over a nonimmune control, by 90% or more over a nonimmune control, or by 100% or more over a nonimmune control.

Vaccine preparation is a well-developed art and general guidance in the preparation and formulation of vaccines is readily available from any of a variety of sources. One such example is New Trends and Developments in Vaccines, edited by Voller et al., University Park Press, Baltimore, Md., U.S.A. 1978.

The vaccine compositions of the present disclosure may also contain other compounds, which may be biologically active or inactive. For example, one or more immunogenic portions of other tumor antigens may be present, either incorporated into a fusion polypeptide or as a separate compound, within the vaccine composition. Polypeptides may, but need not, be conjugated to other macromolecules as described, for example, within U.S. Pat. Nos. 4,372,945 and 4,474,757. Vaccine compositions may generally be used for prophylactic and therapeutic purposes.

In one embodiment, the antigen in a vaccine composition is in the form of a peptide, polypeptide, a protein, or immunogenic portion thereof. An "immunogenic portion," as used herein is a portion of a protein that is recognized (i.e., specifically bound) by a B cell and/or T cell surface antigen receptor. Such immunogenic portions generally comprise at least 5 amino acid residues, more preferably at least 10, and still more preferably at least 20 amino acid residues of an antigenic protein or a variant thereof.

Immunogenic portions of antigen polypeptides may generally be identified using well known techniques, such as those summarized in Paul, *Fundamental Immunology,* 3rd ed., 243-247 (Raven Press, 1993) and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a protein is a portion that reacts with such antisera and/or T cells at a level that is not substantially less than the reactivity of the full length polypeptide (e.g., in an ELISA and/or T cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

In some embodiments, the antigen is a hapten, a hapten conjugated to a carrier protein, polypeptide or other polymer, or derivatives thereof. Haptens include small molecules that can elicit an immune response, predominantly only when attached to a large carrier such as a protein. The hapten may be linked to a carrier protein and a further moiety. Exemplary haptens are aniline, o-, m-, and p-aminobenzoic acid, quinone, histamine-succinyl-glycine (HSG), hydralazine, halothane, indium-DTPA, fluorescein, biotin, digoxigenin, theophylline and dinitrophenol.

Common carrier proteins include serum globulin, albumins, ovalbumin and many others, as well as synthetic polypeptides such as poly-L-glutamic acid. Polysaccharides and liposomes could also be used.

In some embodiments the antigen is an allergen. An allergen includes naturally occurring protein and other small molecules that have been reported to induce allergic, i.e., IgE mediated reactions upon their repeated exposure to an individual. Examples of naturally occurring allergens include pollen allergens (tree, weed, herb and grass pollen allergens), mite allergens (from e.g. house dust mites and storage mites), insect allergens (inhalant, saliva- and venom origin allergens), animal allergens from e.g. saliva, hair and dander from e.g. dog, cat, horse, rat, mouse, etc., fungi allergens and food allergens. Allergens also include drugs, latex In another embodiment, a compound or adjuvant composition described herein may be used in the preparation of DNA-based vaccine compositions. Illustrative vaccines of this type contain DNA encoding one or more polypeptide antigens, such that the antigen is generated in situ. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In one preferred embodiment, the DNA is introduced using a viral expression system (e.g., vaccinia or other pox virus, retrovirus, or adenovirus), which typically involves the use of a non-pathogenic (defective), replication competent virus. Illustrative systems are disclosed, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art.

Alternatively, the DNA may be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads that are efficiently transported into the cells.

Moreover, it will be apparent that a vaccine may contain pharmaceutically acceptable salts of the desired antigens. For example, such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

The adjuvant system may exhibit strong adjuvant effects when administered over a wide range of dosages and a wide range of ratios. The amount of antigen in each vaccine dose is generally selected as an amount which induces an immunoprotective response without significant adverse side effects in typical vaccines. Such amount will vary depending upon which specific immunogen is employed and how it is presented. Of course, the dosage administered may be dependent upon the age, weight, kind of concurrent treatment, if any, and nature of the antigen administered.

The immunogenic activity of a given amount of a vaccine composition can be readily determined, for example by monitoring the increase in titer of antibody against the antigen used in the vaccine composition (Dalsgaard, K. *Acta Veterinia Scandinavica* 69:1-40 (1978)). Another common method involves injecting CD-1 mice intradermally with various amounts of a vaccine composition, later harvesting sera from the mice and testing for anti-immunogen antibody, e.g., by ELISA. These and other similar approaches will be apparent to the skilled artisan.

The antigen can be derived and/or isolated from essentially any desired source depending on the infectious disease, autoimmune disease, condition, cancer, pathogen, or a disease that is to be treated with a given vaccine composition. By way of illustration, the antigens can be derived from viral sources, such as influenza virus, feline leukemia virus, feline immunodeficiency virus, Human HIV-1, HIV-2, Herpes Simplex virus type 2, Human cytomegalovirus, Hepatitis A, B, C or E, Respiratory Syncytial virus, human papilloma virus rabies, measles, or hoof and mouth disease viruses. Illustrative antigens can also be derived from bacterial sources, such as anthrax, diphtheria, Lyme disease, malaria, tuberculosis, *Leishmaniasis, T cruzi*, Ehrlichia, Candida, etc., or from protozoans such as *Babeosis bovis* or Plasmodium. The antigen(s) will typically be comprised of natural or synthetic amino acids, e.g., in the form of peptides, polypeptides, or proteins, can be comprised of polysaccharides, or can be mixtures thereof. Illustrative antigens can be isolated from natural sources, synthesized by means of solid phase synthesis, or can be obtained by way of recombinant DNA techniques.

In another embodiment, tumor antigens may be used in the vaccine compositions for the prophylaxis and/or therapy of cancer. Tumor antigens are surface molecules that are differentially expressed in tumor cells relative to non-tumor tissues. Tumor antigens make tumor cells immunologically distinct from normal cells and provide diagnostic and therapeutic targets for human cancers. Tumor antigens have been characterized either as membrane proteins or as altered carbohydrate molecules of glycoproteins or glycolipids on the cell surface. Cancer cells often have distinctive tumor antigens on their surfaces, such as truncated epidermal growth factor, folate binding protein, epithelial mucins, melanoferrin, carcinoembryonic antigen, prostate-specific membrane antigen, $HER^2$-neu, which are candidates for use in therapeutic cancer vaccines. Because tumor antigens are normal or related to normal components of the body, the immune system often fails to mount an effective immune response against those antigens to destroy the tumor cells. To achieve such a response, the adjuvant systems described herein can be utilized. As a result, exogenous proteins can enter the pathway for processing endogenous antigens, leading to the production of cytolytic or cytotoxic T cells (CTL). This adjuvant effect facilitates the production of antigen specific CTLs, which seek and destroy those tumor cells carrying on their surface the tumor antigen(s) used for immunization. Illustrative cancer types for which this approach can be used include prostate, colon, breast, ovarian, pancreatic, brain, head and neck, melanoma, leukemia, lymphoma, etc.

In one embodiment, the antigen present in the vaccine composition is not a foreign antigen, but a self-antigen, i.e., the vaccine composition is directed toward an autoimmune disease. Examples of autoimmune diseases include type 1 diabetes, conventional organ specific autoimmunity, neurological disease, rheumatic diseases/connective tissue disease, autoimmune cytopenias, and related autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjögren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts.

In one embodiment, the antigen may be covalently bonded to an adjuvant such as the compound of formula I to produce a discrete molecule which may exhibit an enhanced adjuvanting effect on the antigen, which may be greater than the adjuvanting effect attainable in the absence of such covalent bonding, as in a mixture of components (i.e., the antigen and a compound of formula (I)). The covalent bonding can be achieved by reaction through functional groups; for example in the case of the compound of formula I through a carboxylic acid group, a hydroxyl group or an aldehyde functionality. A further enhanced adjuvanting effect may be attained for such covalently-bonded antigen by incorporating a mineral salt adjuvant with such compounds. The mineral salt adjuvant preferably comprises aluminum hydroxide or aluminum phosphate, although other known mineral salt adjuvants, such as calcium phosphate, zinc hydroxide or calcium hydroxide, may be used.

The vaccine compositions may be formulated for any appropriate manner of administration, and thus administered, including for example, topical, oral, nasal, intravenous, intravaginal, epicutaneous, sublingual, intracranial, intradermal, intraperitoneal, subcutaneous, intramuscular administration, or via inhalation. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual vaccine delivery, especially for pediatric applications, or for applications traditionally requiring numerous injections over a prolonged period of time, such as with allergy desensitization therapies.

The vaccine compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, vaccine compositions may be formulated as a lyophilisate. Compounds may also be encapsulated within liposomes using well-known technology.

The vaccine compositions may also comprise other adjuvants or immunoeffectors. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); mineral salts (for example, aluminum, silica, kaolin, and carbon); aluminum salts such as aluminum hydroxide gel (alum), AlK$(SO_4)_2$, AlNa$(SO_4)_2$, AlNH$_4$$(SO_4)$, and Al$(OH)_3$; salts of calcium (e.g., Ca$_3$(PO$_4$)$_2$), iron or zinc; an insoluble suspension of acylated tyrosine; acylated sugars; cationically or anionically derivatized polysaccharides; polynucleotides (for example, poly IC and poly AU acids); polyphosphazenes; cyanoacrylates; polymerase-(DL-lactide-co-glycoside); biodegradable microspheres; liposomes; lipid A and its derivatives; monophosphoryl lipid A; wax D from *Mycobacterium tuberculosis*, as well as substances found in *Corynebacterium parvum*, *Bordetella pertussis*, and members of the genus *Brucella*); bovine serum albumin; diphtheria toxoid; tetanus toxoid; edestin; keyhole-limpet hemocyanin; Pseudomonal Toxin A; choleragenoid; cholera toxin; pertussis toxin; viral proteins; and Quil A. Aminoalkyl glucosamine phosphate compounds can also be used (see, e.g., WO 98/50399, U.S. Pat. No. 6,113,918 (which issued from U.S. Ser. No. 08/853,826), and U.S. Ser. No. 09/074,720). In addition, adjuvants such as cytokines (e.g., GM-CSF or interleukin-2, -7, or -12), interferons, or tumor necrosis factor, may also be used as adjuvants. Protein and polypeptide adjuvants may be obtained from natural or recombinant sources according to methods well known to those skilled in the art. When obtained from recombinant sources, the adjuvant may comprise a protein fragment comprising at least the immunostimulatory portion of the molecule. Other known immunostimulatory macromolecules which can be used include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3, 3'-dicarboxylic acid and 4-nitro-2-aminobenzoic acid (See, Sela, M., *Science* 166: 1365-1374 (1969)) or glycolipids, lipids or carbohydrates.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell-mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145-173.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably, the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation will vary depending upon the site of implantation, the rate and expected duration of release and the nature of the condition to be treated or prevented.

Any of a variety of known delivery vehicles may be employed within pharmaceutical compositions and vaccines to facilitate production of an antigen-specific immune response that targets cells. Delivery vehicles include antigen-presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-target effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

The compositions may comprise a liposome vesicle comprising the compound of formula I. Liposomes are generally produced from phospholipids or other lipid substances. Procedures for the preparation of liposomes are well known to those of skill in the art. Any lipid capable of forming vesicles that comprises the compound of formula I can be employed. For clinical application, it is desirable that the lipid be non-toxic, physiologically acceptable, and metabolizable. Common bilayer forming lipids having clinical potential are phospholipids, fatty acids, sphingolipids, glycosphingolipids, and steroids. Glycerol containing phospholipids are the most commonly used component of liposome formulations having clinical utility. One commonly used example is phosphatidylcholine or lecithin. The steroid cholesterol and its derivatives are often included as components of liposomal membranes. The tendency of liposomes to aggregate and fuse can be controlled by the inclusion of small amounts of acidic or basic lipids in the formulation. The properties of liposomes containing phospholipids are determined by the chemistry of the phospholipid. Important considerations are the hydrocarbon chain length, degree of unsaturation of the hydrocarbon chain, degree of branching of the hydrocarbon chain, and temperature of the system.

Multilamellar liposomes can be created by depositing a mixture of lipids as a thin film by evaporation under reduced pressure followed by dispersion with an excess volume of aqueous buffer containing the antigen with or without organic solvents. Another method is to mix the aqueous phase containing the antigen with small unilamellar liposomes followed by lyophilization. The multilamellar liposomes are formed when the lyophilized product is rehydrated, usually with a small amount of distilled water. The small unilamellar liposomes to be used in this process are produced by dispersing the lipids in an aqueous medium followed by a mechanical means of dispersion such as sonication, use of a high-pressure device, or a solvent injection method. Large and intermediate sized unilamellar liposomes can also be produced by conventional techniques including detergent dialysis, extrusion through small pore size membranes under high pressure, freeze thawing followed by slow swelling, dehydration followed by rehydration and dilution, or dialysis of lipids in the presence of chaotropic ions. The size of the liposomes can be made more uniform by fractionation procedures such as centrifugation or size exclusion chromatography, homogenization, or capillary pore membrane extrusion.

4. METHODS OF USE

The disclosed compounds and compositions may be used in various methods, including methods for modulating an immune response in a subject, methods of inducing or enhancing immunogenicity of an antigen in a subject, and methods of treating, preventing or reducing the susceptibility to an allergy, an autoimmune condition, cancer or a bacterial, viral or prion infection.

a. Modulating Immune Response

The disclosed compounds and compositions may be used in methods of modulating the immune response in a subject, comprising administering to the subject an effective amount of a compound described herein, an adjuvant composition described herein, a vaccine composition described herein, or a pharmaceutical composition described herein.

In some embodiments, the immune response in the subject is increased. In some embodiments, the subject is suffering from cancer, an autoimmune disorder, an allergy or an infectious disease. The infection disease may be caused by a virus, a bacteria or a prion or prion-like protein.

The disclosed compounds and compositions may be used in a method of inducing an enhanced immune response in a subject.

The enhanced immune response may be induced by co-administering the compound or composition with an antigen. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

b. Inducing or Enhancing Immunogenicity of an Antigen

The disclosed compounds and compositions may be used in methods of inducing or enhancing immunogenicity of an antigen in a subject, comprising administering to the subject a vaccine composition comprising the antigen and an adjuvant composition comprising an effective amount of a compound or composition described herein.

Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed. In some embodiments, the antigen is derived from a bacterium, virus, bacteriophage, fungus, prion, neoplasm, autoantigen, animal, plant, recombinant or synthetic material.

c. Methods of Treating, Preventing, or Reducing the Susceptibility to a Disease and Disorder The disclosed compounds and compositions may be used in methods of treating, preventing, or reducing the susceptibility to a disease or disorder, the methods comprising administering to a subject in need thereof a therapeutically effective amount of a compound or a composition described herein.

i. Allergy

In some embodiments, the disease or disorder is an allergy or allergic disease/condition. An allergy refers to acquired hypersensitivity to a substance (allergen). Allergic conditions include, for example, eczema, allergic rhinitis or coryza, hay fever, bronchial asthma, urticaria (hives) and food allergies, and other atopic conditions.

The method may reduce, inhibit, or stop/prevent an allergic reaction or an inflammatory response (e.g., slowing or halting antibody production or amount of antibodies to a specific antigen).

ii. Autoimmune Condition

In some embodiments, the disease or disorder is an autoimmune conditions. Autoimmune conditions result when an individual's immune system attacks its own organs or tissues, producing a clinical condition associated with the destruction of that tissue, Autoimmune conditions include, for example, rheumatoid arthritis, insulin-dependent diabetes mellitus, acquired immunodeficiency syndrome ("AIDS"), hemolytic anemias, rheumatic fever, Crohn's disease, Guillain-Barre syndrome, psoriasis, thyroiditis, Graves' disease, myasthenia gravis, glomerulonephritis, autoimmunehepatitis, multiple sclerosis, and systemic lupus erythematosus. The method may reduce, inhibit, or stop an autoimmune response.

iii. Infection or Infectious Disease

In some embodiments, the disease or disorder is an infection or infectious disease. Infectious diseases are caused by are caused by infectious agents including but not limited to viruses, bacteria, fungi, protozoa, parasites and prion or prion-like proteins. In some embodiments, the infectious disease or infection may be caused by a bacteria, a virus or a prion or prion-like protein.

Viral diseases that can be treated by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), dengue, ebola, zika, rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Bacterial diseases that can be treated by the methods of the present invention include, but are not limited to, mycobacteria rickettsia, mycoplasma, Neisseria, cholera, gonorrhea, Lyme disease, pertussis, plague, syphilis, tuberculosis, Rocky Mountain Spotted Fever, and legionella.

iv. Cancer

In some embodiments, the disease or disorder is cancer. The method may reduce or inhibit the proliferation of cancer cells. The methods can be used with any cancer cell or in a subject having any type of cancer, for example those described by the National Cancer Institute. Exemplary cancers may include the following:

digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

eye cancers such as intraocular melanoma; and retinoblastoma;

musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

breast cancer such as breast cancer including childhood and male breast cancer and breast cancer in pregnancy;

neurologic cancers such as childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor; Germ cell cancers such as childhood extracranial germ cell tumor; extragonadal germ cell tumor; ovarian germ cell tumor; head and neck cancers such as lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia; chronic myelogenous leukemia; and hairy cell leukemia); a lymphoma (e.g., AIDS-related lymphoma; cutaneous T cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders);

lung cancer such as non-small cell lung cancer; and small cell lung cancer;

respiratory cancers such as adult malignant mesothelioma; childhood malignant mesothelioma; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

skin cancers such as Kaposi's sarcoma; Merkel cell carcinoma; melanoma; and childhood skin cancer;

AIDS-related malignancies;

other childhood cancers, unusual cancers of childhood and cancers of unknown primary site; and metastases of the aforementioned cancers.

5. KITS

In one aspect, the disclosure provides kits comprising at least one disclosed compound or a pharmaceutically acceptable salt thereof, or a composition comprising the compound or a pharmaceutically acceptable salt thereof, and one or more of:

(a) at least one antigen;
(b) at least one additional therapeutic agent; and
(c) instructions for administering the compound or composition.

In some embodiments, the at least one disclosed compound and the at least one antigen or the at least one additional therapeutic agent are co-formulated. In some embodiments, the at least one disclosed compound and the at least one antigen or the at least one additional therapeutic agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

The disclosed kits can be employed in connection with disclosed methods of use.

The kits may further include information, instructions, or both that use of the kit will provide increased immunity against certain pathogens in mammals (particularly humans). The information and instructions may be in the form of words, pictures, or both, and the like. In addition or in the alternative, the kit may include the compound, a composition, or both; and information, instructions, or both, regarding methods of administration of compound, or of the composition, preferably with the benefit of treating or preventing medical conditions in mammals (e.g., humans).

The compounds and processes of the disclosure may be better understood by reference to the following examples, which are intended as an illustration of and not a limitation upon the scope of the disclosure.

6. EXAMPLES

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Abbreviations used in the Schemes and descriptions that follow include the following: DCC is N,N'-dicyclohexylcarbodiimide; DMAP is N,N-dimethylpyridin-4-amine; DMF is dimethylformamide; eq is equivalents; IFNα is interferon alpha; IgG is immunoglobulin G; IL-12p70 is interleukin 12 p70; Im-OTf is imidazolium trifluoromethanesulfonate; Pal is $C(O)(CH_2)_{14}CH_3$; PBMC is peripheral blood mononuclear cell; PEG is polyethylene glycol; PMB is para-methoxybenzyl; rt is room temperature; TBAI is tetrabutylammonium iodide; TEA is trimethylamine; THF is tetrahydrofuran; TLR is toll-like receptor; TNFα is tumor necrosis factor alpha; 14Dp1 is 14 days post-primary immunization; and 14Dp2 is 14 days post-secondary immunization.

Example 1. Exemplary Synthesis for Compound UM-1007

A. Synthesis of PEGylated Glycerol

The requisite dipalmitoyl PEGylated glycerol 5 was prepared in 5 steps from commercially available triethyleneglycol monochloride (1).

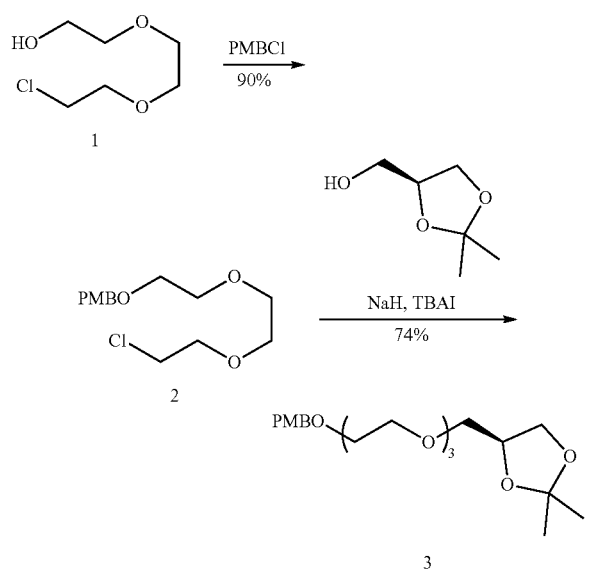

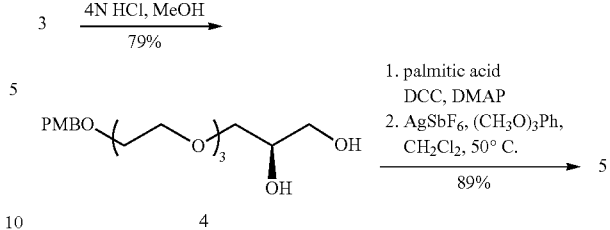

p-Methoxybenzyl chloride (3 eq) and tetra-n-butylammonium iodide (0.02 eq) were added to a solution of 1 in anhydrous D1VIF (2.0 M) and the solution cooled to 0° C. Sodium hydride (1.25 eq) was slowly added to the cold solution. After stirring at 0° C. for 30 min, the reaction mixture was allowed to warm up to rt. After 4 h, the reaction mixture was slowly quenched with a saturated solution of sodium bicarbonate and extracted with chloroform. The organic layer was dried over sodium sulfate, filtered and concentrated under vacuum. The crude was purified by chromatography on silica gel (10 to 40% ethyl acetate in heptane) to give 2 as a colorless oil in 90% yield. Sodium hydride (1.5 eq) was slowly added to a solution of 2 (1.5 eq), 1,2-sn-isopropylidene glycerol (1.0 eq) and tetra-n-butylammonium iodide (0.05 eq) in anhydrous THF (0.69 M). After 15 h at 75° C. additional 2 (0.5 eq) and sodium hydride (1.5 eq) were added and the reaction mixture stirred at 75° C. After 6 hours, the reaction mixture was cooled to rt, quenched by addition of brine and extracted three times with ethyl acetate. The combined organic layers were dried over sodium sulfate, filtered and concentrated under vacuum. The crude was purified by chromatography on silica gel (20 to 80% ethyl acetate in heptane) to give 3 as a colorless oil in 74% yield. 0.4 N HCl was added to a solution of 3 in methanol (0.32 M; $CH_3OH$:HCl 29/1 v/v) and the reaction mixture stirred at rt. After 1 h, the reaction mixture was quenched with a saturated solution of sodium bicarbonate and extracted with chloroform. The organic layer was dried over sodium sulfate, filtered and concentrated under vacuum. The crude was purified by chromatography on silica gel (0 to 12% methanol in chloroform) to give 4 as a colorless oil in 79% yield. DCC (2.1 eq) and DMAP (0.05 eq) were added to a cold (0° C.) solution of 4 and palmitic acid (2.1 eq) in $CH_2Cl_2$ (0.29 M) and the reaction mixture stirred at 0° C. After 30 min, the reaction mixture was allowed to warm up to rt. After 15 h at rt, additional palmitic acid (0.5 eq) and DCC (0.5 eq) were added and stirring continued for 24 h. The reaction mixture was filtered and the crude partially purified by chromatography on silica gel (0 to 50% ethyl acetate in heptane). A solution of the partially purified crude and trimethoxybenzene (0.5 eq) in anhydrous $CH_2Cl_2$ (0.17 M) prepared under nitrogen was cannulated to a solution of silver hexafluoroantimonate(V) (0.05 eq) in anhydrous $CH_2Cl_2$ (0.09 M) under nitrogen. After 2 days at rt, additional silver hexafluoroantimonate(V) (0.05 eq) and trimethoxybenzene (0.5 eq) were added and the reaction mixture stirred at 50° C. 24 h later, the reaction mixture was concentrated under vacuum and purified by chromatography on silica gel (10 to 70% ethyl acetate in heptane) to give 5 as a white solid in 89% yield. $^1$H NMR ($CDCl_3$, 400 MHz), δ 5.23 (m, 1H), 4.34 (dd, 1H), 4.16 (dd, 1H), 3.50-3.74 (m, 14 H), 2.49 (t, 1H), 2.30 (dd, 4H), 1.60 (m, 4 H), 1.25 (m, 48H), 0.88 (t, 6H).

B. Synthesis of Compound UM-1007

The oxadenine UM-1007 was prepared by phospholipidation of core oxadenine 8 with a solution of phosphoramidite 7 generated in-situ from 5 as shown below, using the tandem method previously developed (*Tetrahedron Lett.*, 2016, 57, 2063-2066).

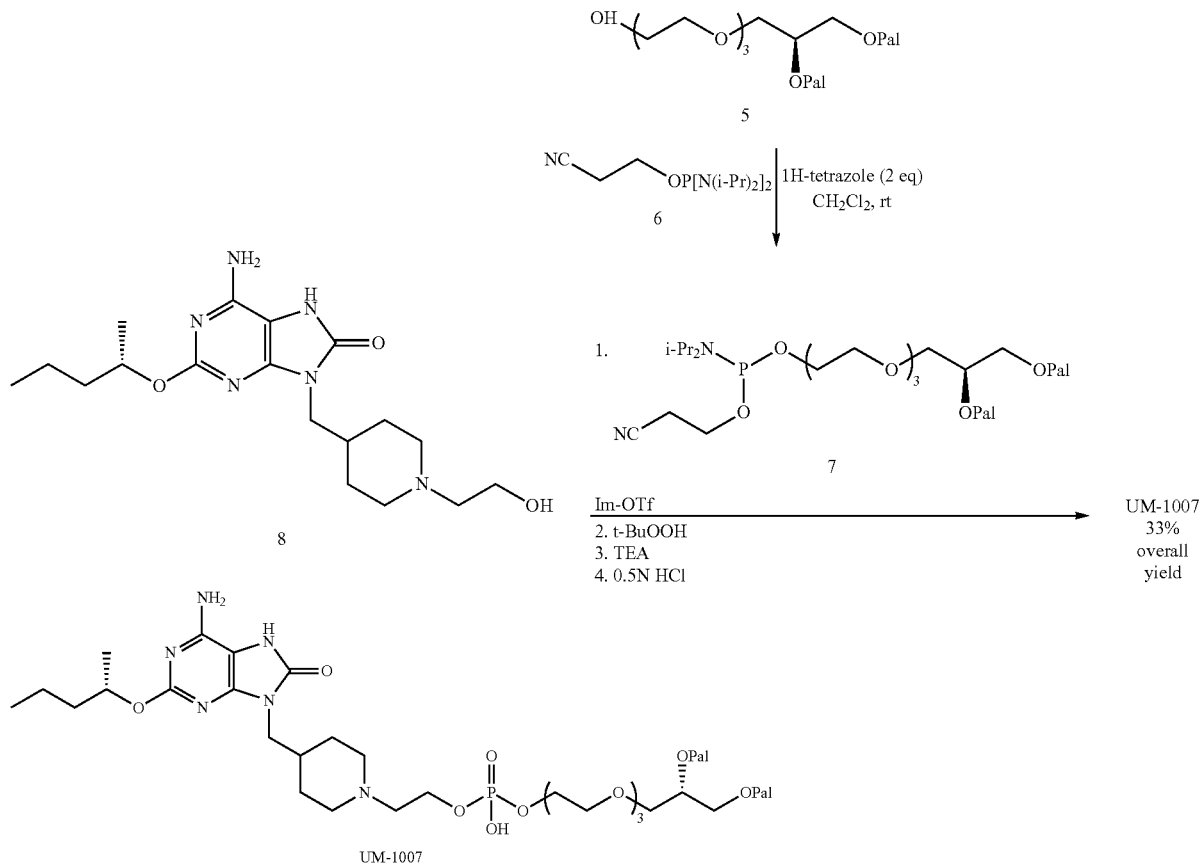

Commercially available phosphordiamidite 6 (1.3 eq) was added to a solution of dipalmitoyl PEGylated glycerol 5 (1.3 eq) in anhydrous methylene chloride (0.12 M) under nitrogen followed by slow addition of tetrazole (1.5 eq). After stirring at rt for 1 h, the reaction mixture was cooled to 0° C. and oxoadenine 8 (1.0 eq) and imidazolium triflate (2.0 eq) were added The reaction mixture was stirred at 0° C. for 10 min then allowed to warm up to rt. After 1 h, the reaction mixture was quenched by addition of a saturated solution of sodium bicarbonate. The organic layer was dried over sodium sulfate and concentrated to provide a crude phosphite. t-Butyl hydroperoxide (5.5 M in nonane, 2.0 eq) was added to a solution of crude phosphite in anhydrous methylene chloride (0.12 M). After 30 min at rt, the reaction mixture was concentrated under vacuum and dissolved in acetonitrile/triethylamine (2.8:1 v/v, 0.05 M) and the reaction mixture stirred at rt overnight. After concentration under vacuum, the reaction mixture was purified by chromatography on silica gel (20-100% methanol/acetonitrile (50/50) in chloroform) to give UM-1007 in 36% overall yield. $^1$H NMR (400 MHz, CDCl$_3$/CD$_3$OD) δ 5.20 (m, 1H), 5.12 (m, 1H), 4.35 (dd, 1H), 4.12-4.17 (m, 3H), 4.05 (q, 2H), 3.79 (br s, 2H), 3.59-3.70 (m, 12H), 3.26 (br s, 2H), 2.80 (br s, 1H), 2.32 (q, 4H), 1.95 (m, 2H), 1.77 (m, 2H), 1.58 (m, 4H), 1.42 (m, 2H), 1.26 (m, 51H), 0.88 (m, 9H). $^{13}$C NMR (100 MHz, CDCl$_3$/CD$_3$OD) δ 174.2, 173.9, 160.7, 153.9, 149.9, 148.5, 106.4, 98.8, 77.8, 73.2, 71.1, 70.9, 70.8, 70.7, 70.5, 70.3, 69.7, 65.4, 65.3, 63.1, 58.8, 53.3, 47.0, 38.6, 34.6, 34.4, 32.2, 29.9, 29.8, 29.6, 29.4, 29.3, 27.4, 25.2, 25.1, 22.9, 20.0, 19.0, 18.9, 14.2, 14.1, 8.8. HRMS [M+H] calcd 1141.7868, found 1141.7906.

Example 2. Biological Activity

A. In Vitro Activity of Compound UM-1007

IFNα and IL-12p70 responses were measured in primary human peripheral blood mononuclear cells (PBMCs) after exposure to various concentrations of oxoadenine compounds.

Liposomes were prepared using the thin film method: phospholipids (DOPC and cholesterol at 40 and 10 mg/mL respectively) and agonist(s) (TLR7/8 agonist fixed at 2 mg/mL) were dissolved in chloroform at the desired concentration in a round bottom flask. The solvent was removed under vacuum by rotary evaporation at 45° C., and the resulting dried film was placed in a vacuum chamber overnight to remove any residual solvent. Rehydration buffer was added to the dried film and the suspension was sonicated to resuspend the phospholipids and form the unilamellar vesicles. Sonication continued until the particle size was<200 nm, at which time the formulations were sterile filtered through a 0.22 μm PVDF filter. Concentrations of agonist(s) in the formulations was determined by RP-HPLC using a five-point standard curve. Human whole blood was collected from normal healthy donors at the University of Montana (Missoula, MT) using an Institutional Review Board approved protocol. Peripheral blood mononuclear cells (PBMCs) were isolated via a Ficoll Hypaque 1.077 gradient separation and cultured at $0.5 \times 10^6$ cells/well in 96-well tissue culture plates with RPMI-1640 media (HyCone™, Logan, UT), Pen/Strep/Glutamine (HyCone™, Logan, UT) and 10% heat inactivated FBS (Corning, Manassas, VA). Human PBMCs were stimulated for 24 h with increasing concentrations of the indicated compounds. Culture supernatants were analyzed for IL-12p70 and IFNα levels using human IL-12p70 DuoSet (R) ELISA kit (R&D Systems, Minneapolis, MN) and human IFNα VeriKine ELISA kit (Pestka Biomedical Laboratories, Inc., Piscataway, NJ).

Figure 2A:
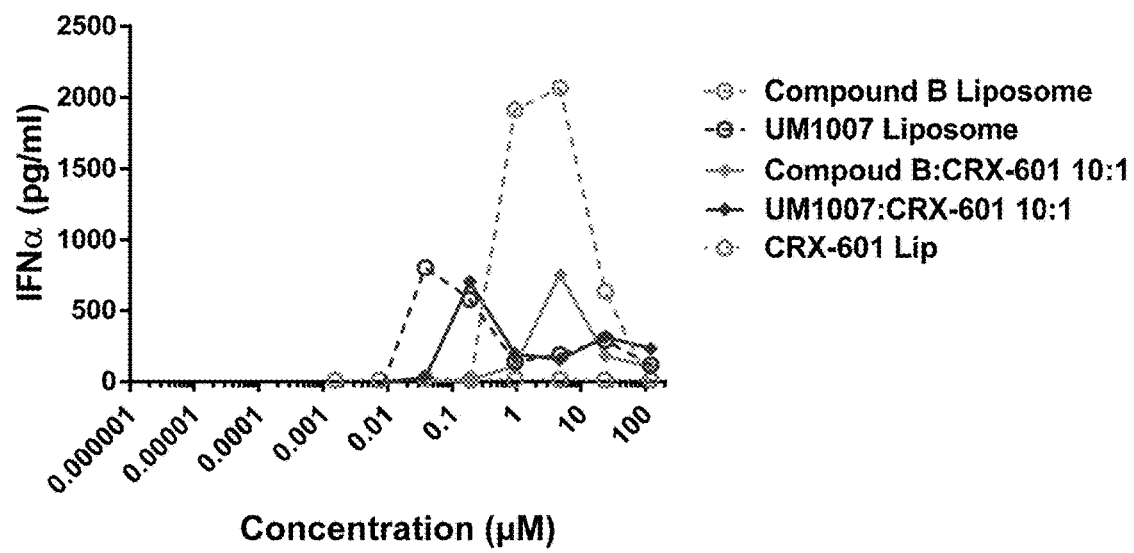
FIG. 2A and FIG. 2B are graphs of the INFα (FIG. 2A) and IL-12p70 (FIG. 2B) responses in the supernatants from human PBMCs stimulated with varying concentrations of select TLR agonist compounds.

The PEGylated oxoadenine UM-1007 was a more potent IFNα inducer in human PBMC than the corresponding non-PEGylated oxoadenine (Compound B) (see FIG. 1 for structure), when tested alone or in combination with the TLR4 agonist CRX-601, indicating that the introduction of a PEGylated linker increased IFNα induction (FIG. 2A).

Figure 2B:
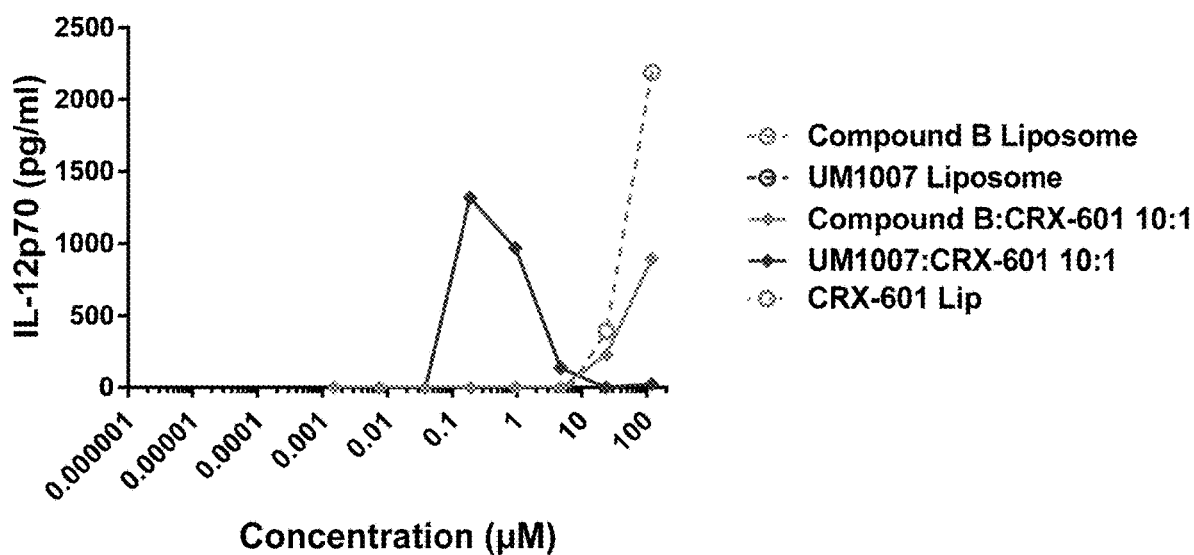

While the non-PEGylated oxoadenine (Compound B) induced IL-12p70 by itself at high dose (>10 μM), the PEGylated oxoadenine UM-1007 was a much more potent IL-12p70 inducer (125-fold) in human PBMC than the corresponding non-PEGylated oxoadenine (Compound B) when combined with the TLR4 agonist CRX-601, indicating that the introduction of a PEGylated linker increased synergy with TLR4 agonists for IL-12p70 induction (FIG. 2B).

B. In Vivo Activity of Compound UM-1007

Murine studies were carried out in an OLAW and AAALAC accredited vivarium in accordance with University of Montana's IACUC guidelines for the care and use of laboratory animals. Balb/c mice (10/group) received two intramuscular immunizations with increasing doses of adjuvant (3 different doses) and monovalent (A/Victoria, H3N2) split flu antigen (0.15 μg) on day 0 and day 14. Serum was harvested 14 days' post primary (14Dp1) and 14 days' post-secondary immunizations (14Dp2) for antibody analysis by ELISA. ELISA plates were coated with 100 μL of detergent-split A/Victoria influenza vaccine at 1 μg/mL. Following washing (PBS plus tween 20) and blocking (SuperBlock, Scytek Laboratories), plates were incubated with diluted serum for 1 hr followed by anti-mouse IgG, IgG1 or IgG2a-HRP secondary antibody (Bethyl Laboratories) and TMB substrate (BD). Plates were read at 450 nm. Antibody titers were determined by calculating titer of each sample at OD 0.3.

Porcine studies were carried out by PAIRimmune (Laval, Canada), a contract service laboratory. Serum of Yucatan minipigs (5/groups) was harvested at day −21 and day −1 for the evaluation of pre-existing anti-influenza serum antibody titers. These pigs exhibited some low-level pre-existing anti-influenza serum antibody titers. Pigs received two intramuscular immunizations (500 μL/dose) with adjuvants (2 different doses) and split flu antigen (1/10 of human dose) on day 0 and day 21. Serum was harvested 14 days' post primary (14Dp1) and 14 days' post-secondary immunizations (14Dp2) for antibody analysis. ELISA plates were coated with 100 μL of detergent-split A/Victoria influenza vaccine at 1 μg/mL. Following washing (PBS plus tween 20) and blocking (SuperBlock, Scytek Laboratories), plates were incubated with diluted serum for 1 hr followed by anti-pig IgX-HRP conjugated secondary antibodies and TMB substrate. Plates were read at 450 nm. Antibody titers were determined by calculating titer of each sample at OD 0.3.

Figure 3A:
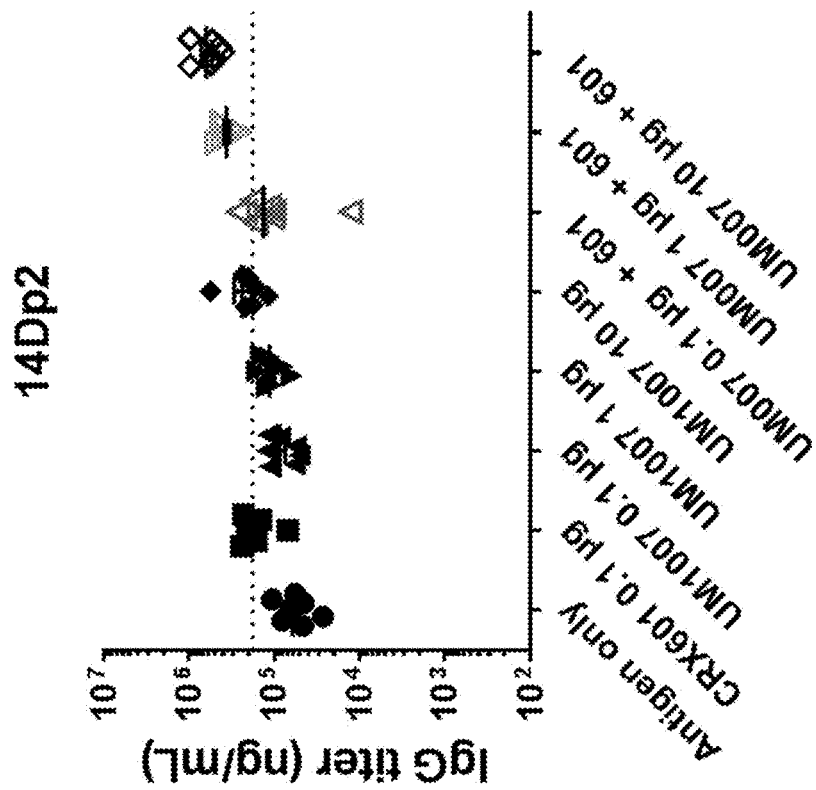
FIG. 3A, FIG. 3B, FIG. 3C and FIG. 3D are graphs of antigen-specific IgG (FIGS. 3A-3B) and IgG2A (FIGS. 3C-3D) titers observed in a murine split-flu study conducted with varying concentrations of liposomal formulation of CRX-601, UM-1007, or co-encapsulated CRX-601 and UM-1007. Values were recorded 14 days following a single intramuscular vaccination in naïve mice (14dp1, FIGS. 3A, 3C) and after administration of a second booster vaccination (14dp2, FIGS. 3B, 3D).
Figure 3B:
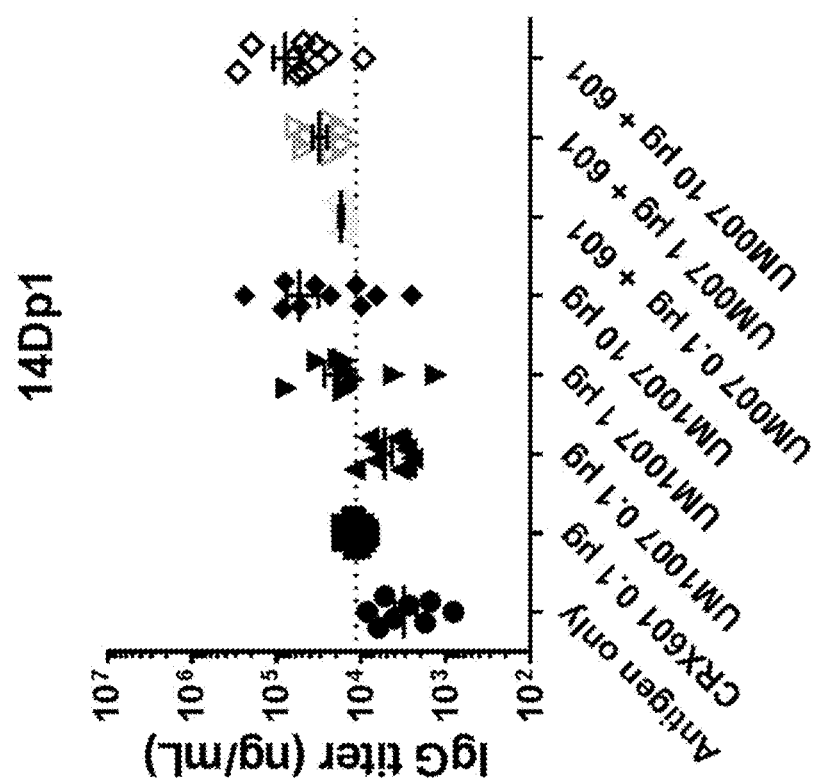
Figure 3D:
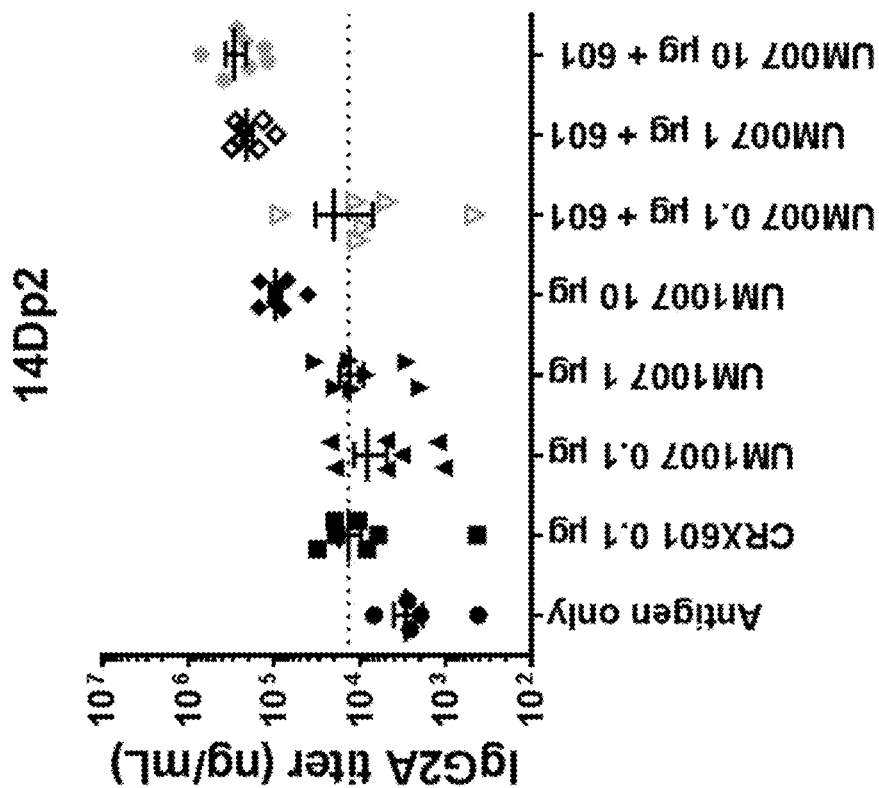
Figure 3C:
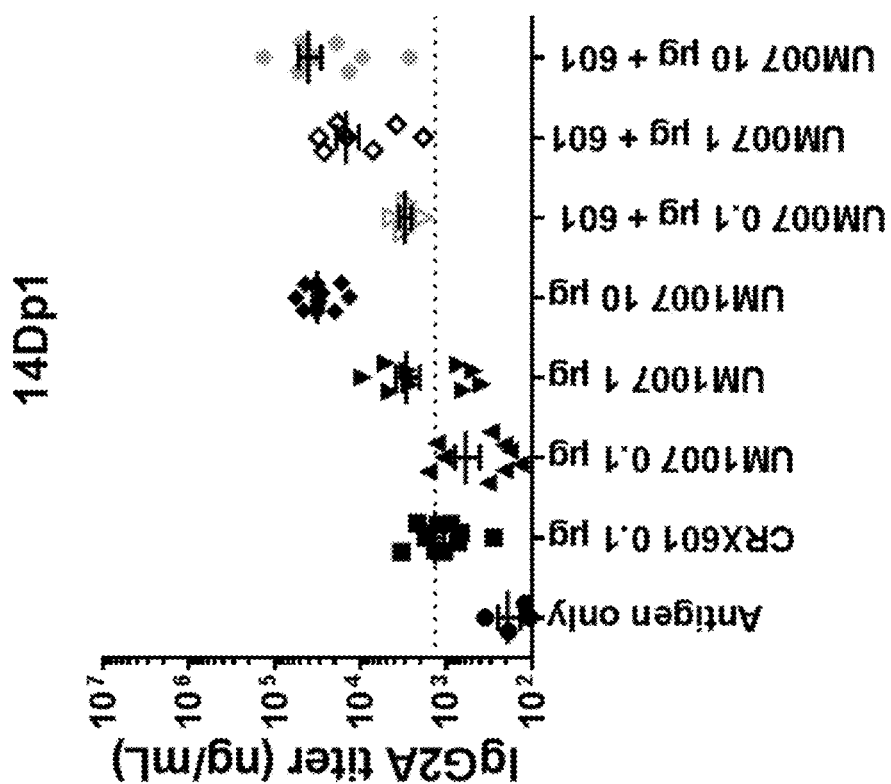

In a murine split-flu study, UM-1007 was formulated in liposomes, alone or co-encapsulated with the TLR4 agonist CRX-601 at a fixed TLR7/8:TLR4 ratio of 10:1. Strong anti-influenza IgG titers were detected 14 days following a single intramuscular vaccination in naïve mice (14dp1, FIG. 3A). Titers were additionally enhanced by administration of a second booster vaccination (14dp2, FIG. 3B). UM-1007 enhanced titers in a dose-dependent manner with 10 μg, displaying 17-fold higher titers over antigen-only vaccinated animals. When co-encapsulated with CRX-601, this response was further boosted >25-fold over the antigen-alone group.

Figure 4B:
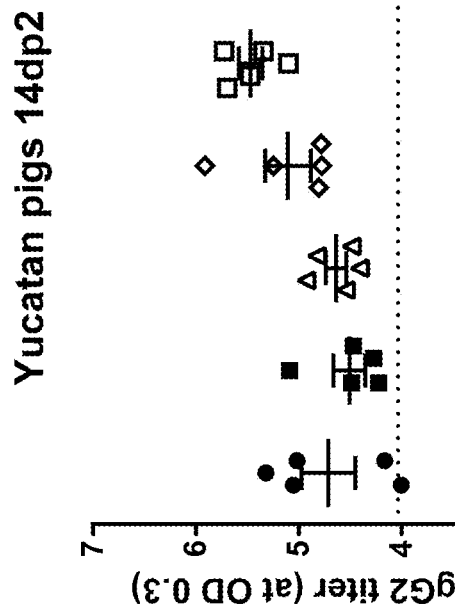
FIG. 4A and FIG. 4B are graphs of IgG1 (FIG. 4A) and IgG2 (FIG. 4B) titers observed in a split-flu study conducted in Yucatan minipigs with varying concentrations of liposomal formulations of CRX-601, UM-1007, or co-encapsulated CRX-601 and UM-1007. Values were recorded 14 days post-administration of a booster vaccination (14dp2).
Figure 4A:
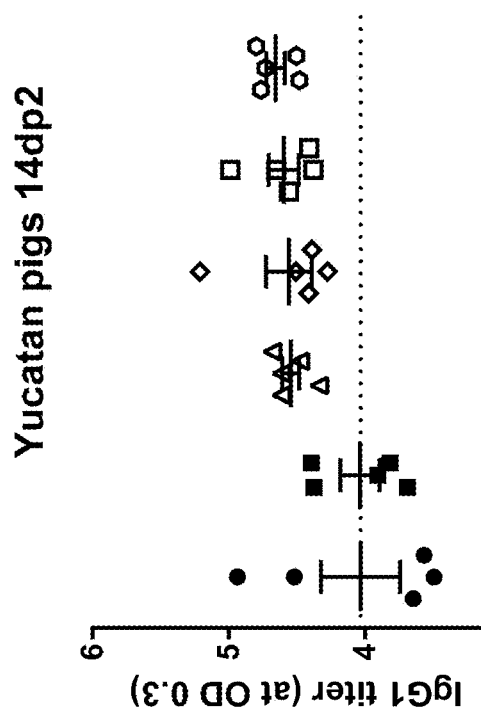

UM-1007 was also evaluated as a flu vaccine adjuvant in Yucatan minipigs. UM-1007 was formulated in liposomes, alone or co-encapsulated with the TLR4 agonist CRX-601. Admixed UM-1007 liposomes and CRX-601 liposomes were also evaluated. The pigs used in this experiment exhibited some pre-existing anti-influenza serum antibody titers. Regardless, all TLR7/8-TLR4 agonists adjuvanted groups demonstrated higher average antibody titers than the antigen-alone group following a single (not shown) or booster vaccination (14dp2, FIG. 4). Increases in influenza-specific IgG1 (FIG. 4A) and IgG2 (FIG. 4B) were clearly demonstrated for co-encapsulated UM-1007 and CRX-601 in comparison to either CRX-601 or UM-1007 alone.

C. Effect of Acyl Side Chains on In Vitro Activity of Selected TLR Agonists

Figure 5A:
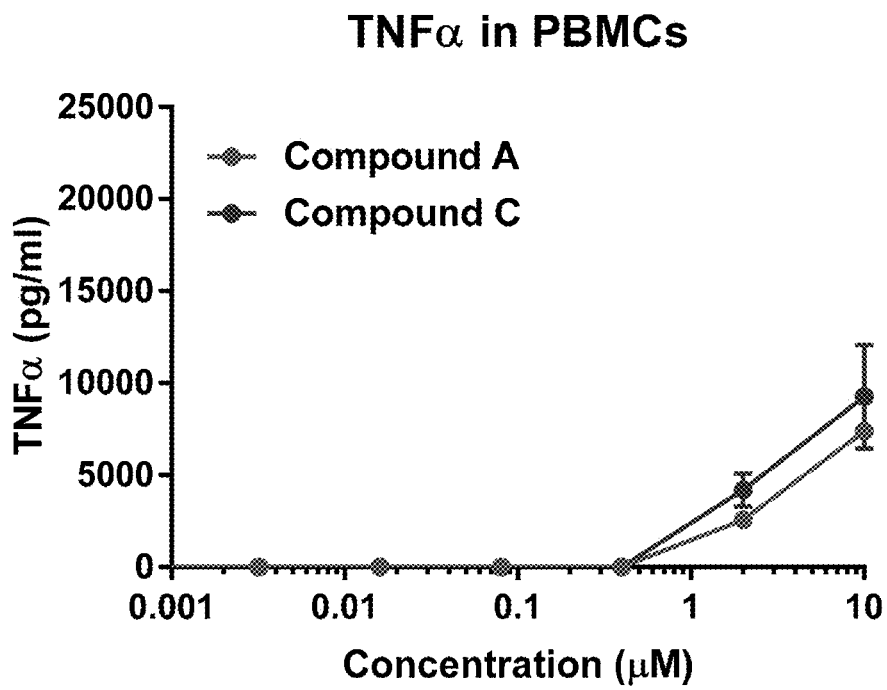
FIG. 5A, FIG. 5B and FIG. 5C are graphs of TNFα (FIG. 5A), INFα (FIG. 5B), and IL-12p70 (FIG. 5C) responses in the supernatants from human PBMCs stimulated with varying concentrations of TLR agonists CRX-601, Compound A, and Compound C.
Figure 5B:
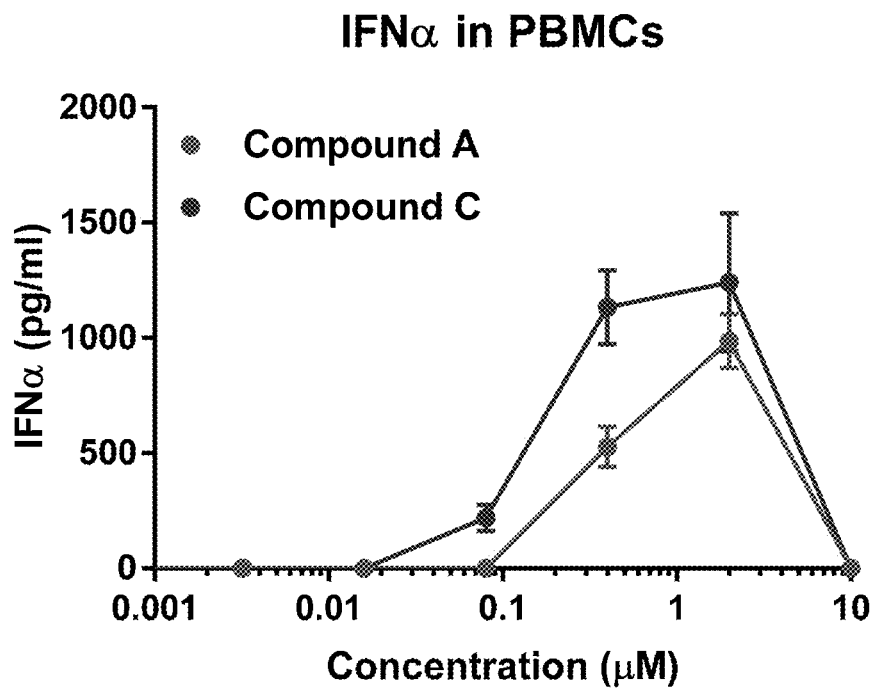
Figure 5C:
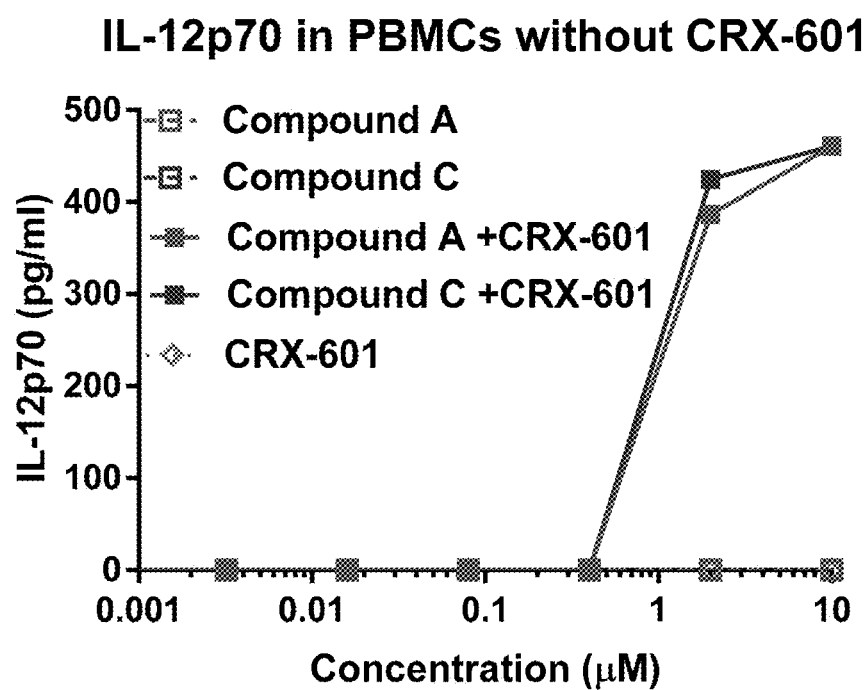

Compound B has oleoyl acyl chains while UM-1007 has palmitoyl acyl chains (FIG. 1). The increase of in vitro activity observed above for UM-1007 vs Compound B was not due to the different acyl chains, as shown when the activity of the palmitoyl oxoadenine Compound C versus the oleoyl oxoadenine Compound A was compared (FIG. 5). Both oxoadenines induced similar levels of TNFα (FIG. 5A.), IFNα (FIG. 5B) (a slight activity increase was observed for the palmitoyl oxoadenine) and IL-12p70 (FIG. 5C).

Example 3. Biological Activity

A. In Vivo Activity of Compound UM-1007

Figures 6A, 6B:
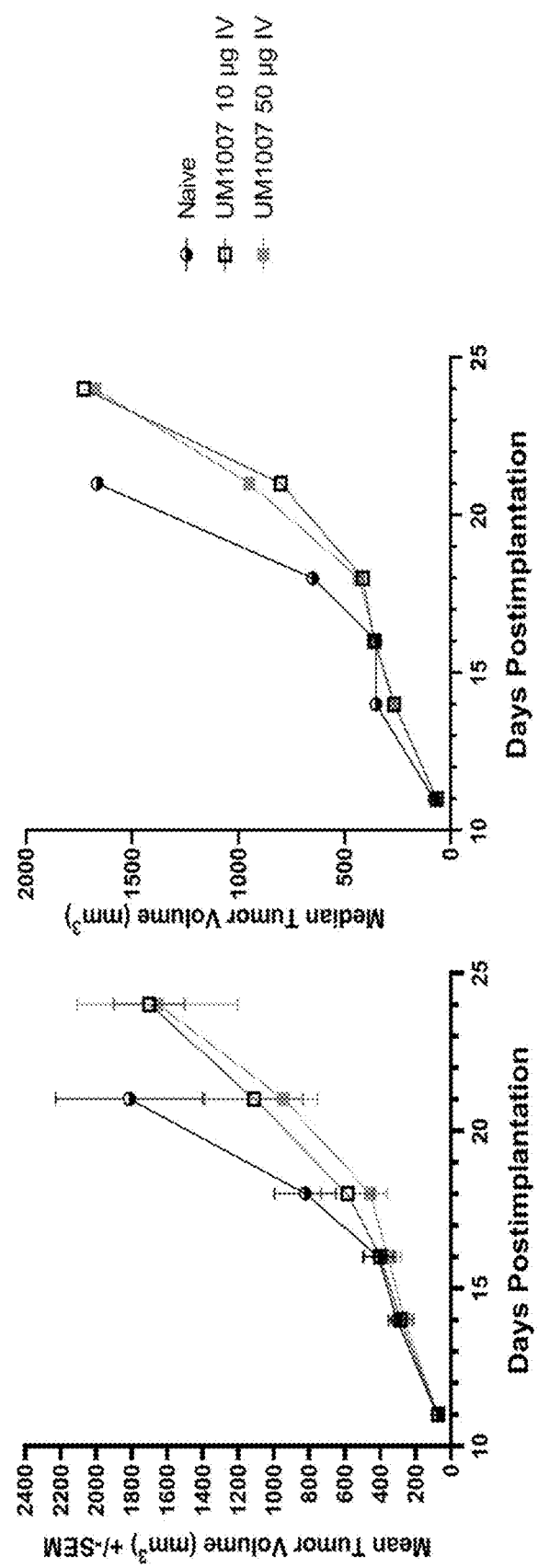
FIG. 6A and FIG. 6B are graphs which show the effects on mean tumor volume and median tumor volume in young, female Balb/c mice after treatment with 10 μg or 50 μg of UM-1007.

Young, female Balb/c mice (approximately 8 weeks old) were implanted with $1 \times 10^6$ CT26 cells (murine colon cancer cell line, syngeneic in Balb/c mice) subcutaneously in the right flank. When tumors reached an average size of 75 mm³ (11 days after CT26 cells were implanted), mice were randomized into treatment groups. Beginning on day 12, 10 μg or 50 μg of UM-1007 in an aqueous formulation (2% glycerol in sterile water) was injected IV once a week for two weeks. As shown in FIG. 6A and FIG. 6B, this resulted in slower tumor growth compared to treatment naive controls.

Example 4. Adsorption of UM 1007 to Alum

Materials

Alhydrogel® (10 mg/mL of aluminum) is an aluminum hydroxide wet gel suspension available from InvivoGen. Alhydrogel® particles have a net positive electrical charge at pH 5-7 and suited for adsorption of negatively charged antigens (e.g. antigens with isoelectric points below the pH of formulation).

Adju-Phos® (0.5% of aluminum) is an aluminium phosphate wet gel suspension available from InvivoGen. Adju-Phos® particles have a negative electrical charge at pH 5-7 and suited for adsorption of positively charged antigens (e.g. antigens with isoelectric points above the pH of formulation).

Methods

Preparation of Aqueous Formulation of UM 1007

UM 1007 was salted by platform dry salting procedure using choline bicarbonate. Briefly, UM 1007 was taken in a glass vial and adequate amount of tetrahydrofuran and 0.8 equivalents of choline bicarbonate were added to obtain a clear solution. The mixture was vortexed well and the solvent was evaporated under reduced pressure using Rotary Evaporator. The thin film formed on the walls of the glass vial was rehydrated with 2% glycerol and sonicated using a bath sonicator for 210 minutes at<35° C. to reduce the particle size. The concentration of UM 1007 was estimated using a RP-HPLC method.

Adsorption of UM 1007 to Alhydrogel and Adju-Phos

Adsorption experiments of UM 1007 to Alhydrogel and Adju-Phos was performed at two different weight ratios of UM 1007 to aluminum (1:1 and 1:2 w/w) and 3 different solutions (2% glycerol, water for irrigation (WIFI) and TRIS buffer (pH of 8.1). A series of UM 1007-alum formulations were prepared at room temperature by mixing different amounts of UM 1007 aqueous formulation, the respective stock buffer (2% glycerol, water for irrigation and pH 8.1 TRIS buffer) and aluminum stock (1 mg/mL of Alhydrogel or Adju-Phos). Alhydrogel and Adju-Phos were diluted to 1 mg/mL prior to the experiment. Different volumes of UM 1007 (0.7215 mg/mL) and alum (1 mg/mL) were gently mixed by end-over-end rotation at room temperature for around 1 hour. The samples were centrifuged for 5 minutes at 4,000 rpm and the supernatants were analyzed using a RP-HPLC method to determine the amount of UM 1007 not adsorbed. The percentage of UM 1007 adsorbed on alum was estimated relative to the amount of UM 1007 in the control UM 1007. The results of the study are presented in Table 1.

TABLE 1

Results of UM1007 adsorbed to alum in different conditions

| No | Description of the formulation | Percentage of UM 1007 adsorbed |
|---|---|---|
| 1 | UM 1007 Control in 2% glycerol | 0 |
| 2 | UM 1007:Alyhydrogel (1:2) in 2% glycerol (w/w) | 99.8 ± 0.01 |
| 3 | UM 1007:Alyhydrogel (1:1) in 2% glycerol (w/w) | 82.37 ± 0.64 |

TABLE 1-continued

Results of UM1007 adsorbed to alum in different conditions

| No | Description of the formulation | Percentage of UM 1007 adsorbed |
|---|---|---|
| 4 | UM 1007:Alhydrogel (1:2) in WIFI (w/w) | 99.91 ± 1.4 |
| 5 | UM 1007:Alhydrogel (1:2) in TRIS buffer pH 8.1 (w/w) | 98.28 ± 0.38 |
| 6 | UM 1007:Adju-Phos (1:2) in 2% glycerol (w/w) | 9.20 ± 1.41 |
| 7 | UM 1007:Adju-Phos (1:1) in 2% glycerol (w/w) | 6.50 ± 0.3 |

For reasons of completeness, various aspects of the invention are set out in the following numbered clauses:

Clause 1. A compound of formula (I),

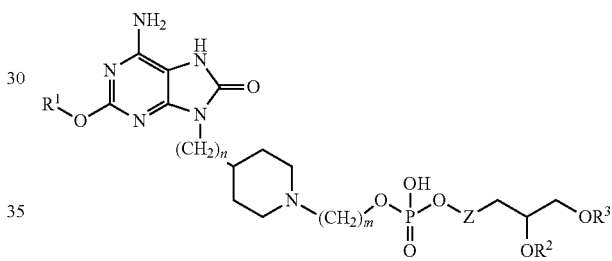

or a pharmaceutically acceptable salt thereof, wherein $R^1$ is $C_1$-$C_8$ alkyl;

$R^2$ is H, $C_6$-$C_{20}$ alkyl, $C_6$-$C_{20}$ alkenyl, or $C(O)R^4$;

$R^3$ is $C_6$-$C_{20}$ alkyl, $C_6$-$C_{20}$ alkenyl, or $C(O)R^4$;

$R^4$, at each occurrence, is independently selected from $C_6$-$C_{20}$ alkyl and $C_6$-$C_{20}$ alkenyl;

n is 1, 2, 3, 4, 5, or 6;

m is 2, 3, 4, 5, or 6;

Z is $(C_2$-$C_6$ alkylene-O$)_q$; and q is 1, 2, 3, 4, 5, 6, 7, 8, 9, 10, 11, 12, 13, 14, 15, 16, 17, 18, 19 or 20.

Clause 2. The compound of clause 1, or a pharmaceutically acceptable salt thereof, wherein $R^2$ is hydrogen or $C(O)R^4$.

Clause 3. The compound of clause 1 or clause 2, or a pharmaceutically acceptable salt thereof, wherein $R^3$ is $C(O)R^4$.

Clause 4. The compound of any one of clauses 1-3, or a pharmaceutically acceptable salt thereof, wherein $R^4$, at each occurrence, is independently selected from $(CH_2)_{10}CH_3$, $(CH_2)_{12}CH_3$, $(CH_2)_{14}CH_3$, $(CH_2)_{16}CH_3$, and $(CH_2)_7CH=CH(CH_2)_7CH_3$.

Clause 5. The compound of any one of clauses 1-4, or a pharmaceutically acceptable salt thereof, wherein $R^4$ is $(CH_2)_{14}CH_3$.

Clause 6. The compound of any one of clauses 1-5, or a pharmaceutically acceptable salt thereof, where n is 1.

Clause 7. The compound of any one of clauses 1-6, or a pharmaceutically acceptable salt thereof, wherein m is 2.

Clause 8. The compound of any one of clauses 1-7, or a pharmaceutically acceptable salt thereof, wherein Z is ($C_2$ alkylene-O)$_q$.

Clause 9. The compound of any one of clauses 1-8, or a pharmaceutically acceptable salt thereof, wherein q is 3, 6, 9, 12, or 16.

Clause 10. The compound of any one of clauses 1-9, or a pharmaceutically acceptable salt thereof, wherein q is 3.

Clause 11. The compound of clause 1, wherein the compound is a compound of formula (Ia):

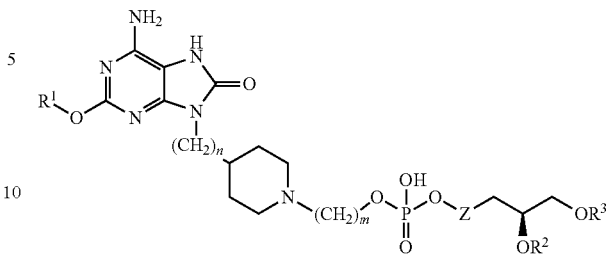

(Ia)

or a pharmaceutically acceptable salt thereof.

Clause 12. The compound of clause 1, or a pharmaceutically acceptable salt thereof, selected from the group consisting of:

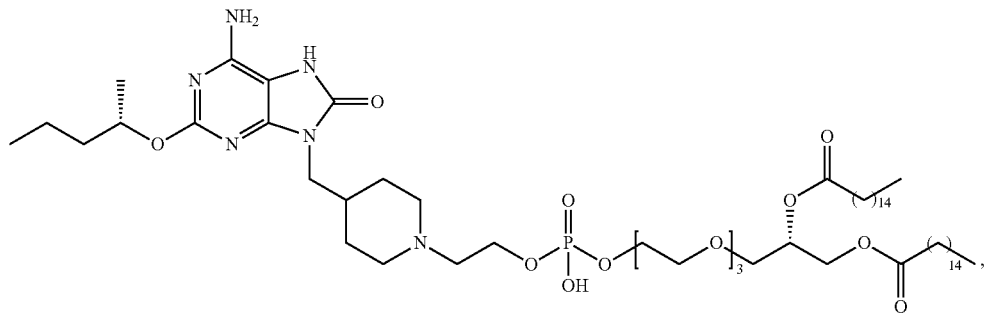

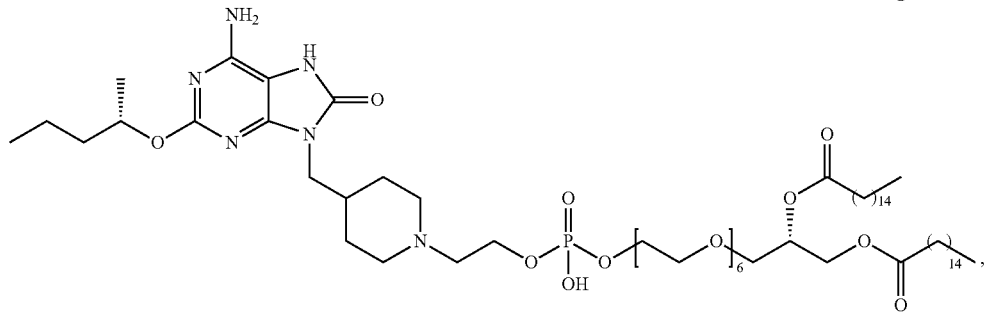

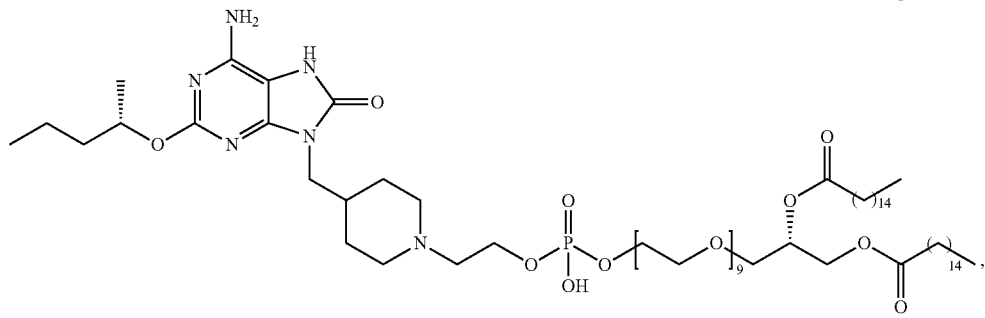

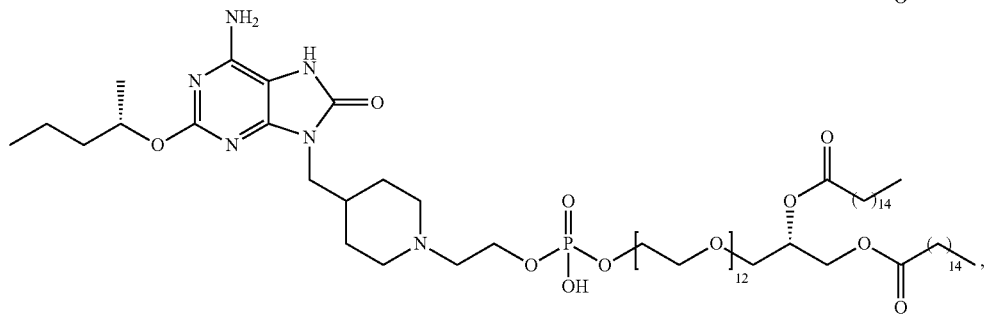

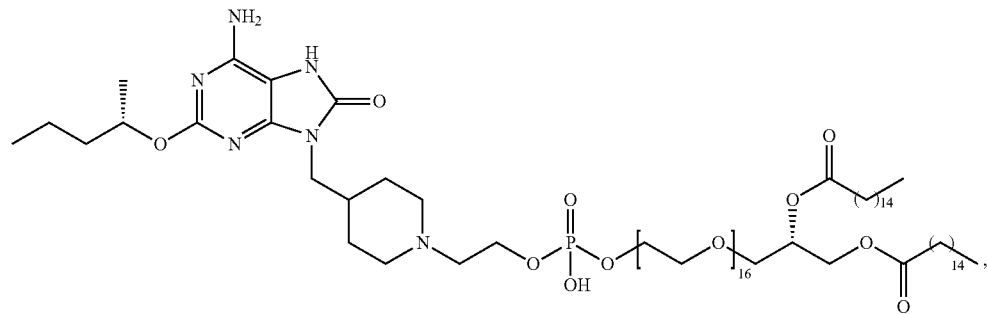
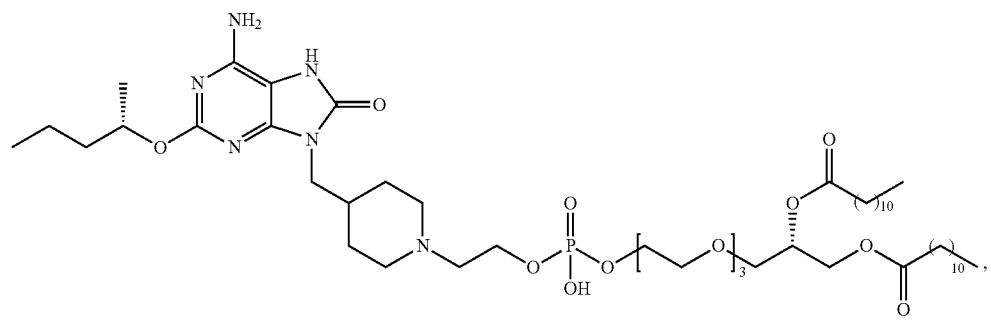
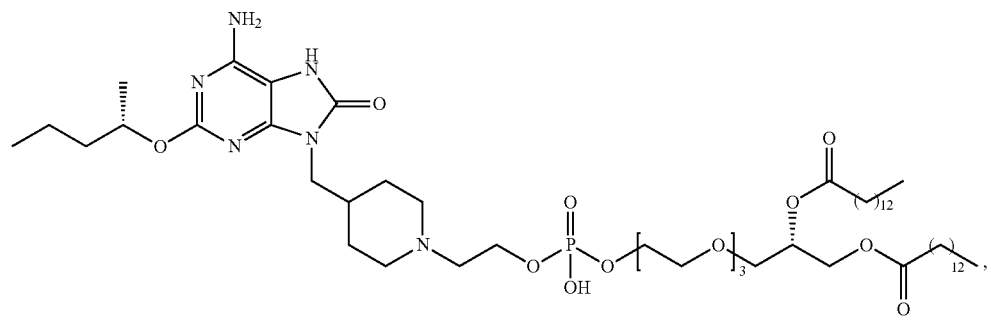
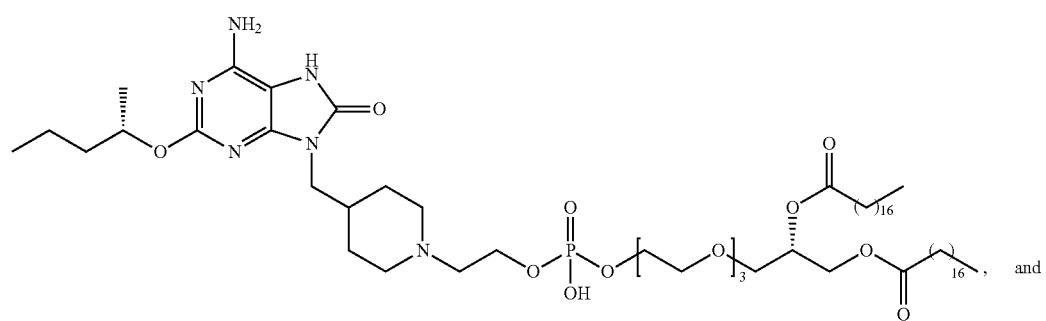
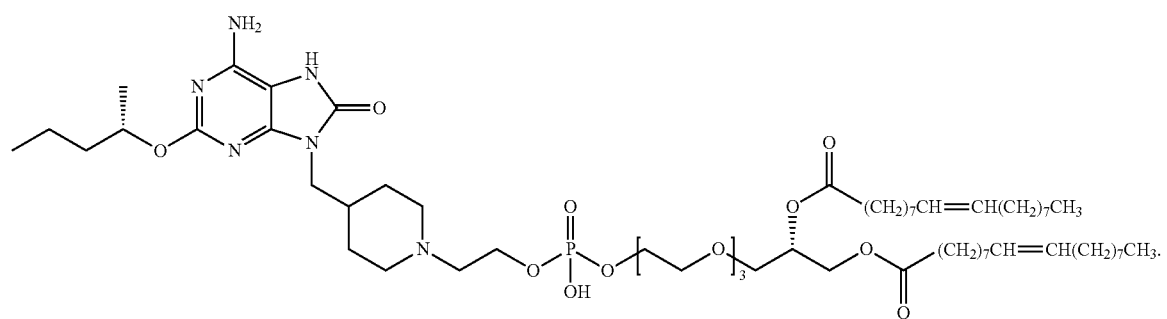

Clause 13. The compound of any one of clauses 1-12, wherein the pharmaceutically acceptable salt is choline salt.

Clause 14. The compound of any one of clauses 1-13, or a pharmaceutically acceptable salt thereof, wherein the compound is a TLR7 antagonist.

Clause 15. The compound of any one of clauses 1-13, or a pharmaceutically acceptable salt thereof, wherein the compound is a TLR8 antagonist.

Clause 16. A formulation comprising a microparticle or nanoparticle comprising the compound of any one of clauses 1-15, or a pharmaceutically acceptable salt thereof.

Clause 17. The formulation of clause 16, wherein the microparticle or nanoparticle comprises a liposome, a micelle, a polymeric particle, a block co-polymer, a silica particle, an emulsion, or a combination thereof.

Clause 18. An adjuvant composition comprising an effective amount of a compound of any one of clauses 1-15, or a pharmaceutically acceptable salt thereof.

Clause 19. The adjuvant composition of clause 18, wherein the adjuvant composition induces a Th1 type immune response.

Clause 20. A method for inducing an enhanced immune response in a subject, comprising administering to said subject an immunogenic composition comprising a compound of any one of clauses 1-15, a pharmaceutically acceptable salt thereof, or the adjuvant composition of clause 18 or clause 19.

Clause 21. A vaccine composition comprising an antigen and a compound of any one of clauses 1-15, a pharmaceutically acceptable salt thereof, or the adjuvant composition of clause 18 or clause 19.

Clause 22. The vaccine composition of clause 21, wherein the antigen is derived from a bacterium, virus, bacteriophage, fungus, prion, neoplasm, autoantigen, animal, plant, recombinant or synthetic material.

Clause 23. The vaccine composition of clause 21 or 22, wherein the antigen is in the form of a peptide or polypeptide.

Clause 24. The vaccine composition of clause 21 or 22, wherein the antigen is in the form of a hapten or hapten conjugated to a carrier protein.

Clause 25. The vaccine composition of clause 21 or 22, wherein the antigen is an allergen.

Clause 26. A method for inducing or enhancing immunogenicity of an antigen in a subject, comprising administering to the subject a vaccine composition of any one of clauses 21-25, or a pharmaceutically acceptable salt thereof, or the adjuvant composition of clauses 18-19.

Clause 27. A pharmaceutical composition comprising an effective amount of a compound of any one of clauses 1-15, or a pharmaceutically acceptable salt thereof.

Clause 28. The pharmaceutical composition of clause 27, further comprising an additional therapeutic agent.

Clause 29. The pharmaceutical composition of clause 28, wherein the additional therapeutic agent is an adjuvant, an immunostimulant, a chemotherapeutic agent, an immune modulatory agent or a combination thereof.

Clause 30. The pharmaceutical composition of clause 29, wherein the adjuvant is a TLR4 ligand.

Clause 31. The pharmaceutical composition of clause 29, wherein the adjuvant is an aluminum salt.

Clause 32. The pharmaceutical composition of clause 31, wherein the compound of any one of claims 1-15 is adsorbed to the aluminum salt.

Clause 33. The pharmaceutical composition of clause 32, further comprising an antigen adsorbed to the aluminum salt with the compound.

Clause 34. The pharmaceutical composition of clause 29, wherein the immune modulatory agent is an immune checkpoint inhibitor, a tumor phagocytosis-inducing agent, or a combination thereof Clause 35. A method of modulating an immune response in a subject, comprising administering to the subject the pharmaceutical composition of any one of clauses 27-34.

Clause 36. The method of clause 35, wherein the immune response in the subject is increased.

Clause 37. The method of clause 35 or 36, wherein the subject is suffering from cancer, an autoimmune disorder, an allergy or an infectious disease.

Clause 38. The method of clause 37 wherein the infectious disease is a viral, bacterial or prion infection.

Clause 39. A method of treating, preventing, or reducing the susceptibility to a disease or disorder in a subject comprising administering to a subject in need thereof a therapeutically effective amount of the compound of any one of clauses 1-15, a pharmaceutically acceptable salt thereof, or the pharmaceutical composition of any one of clauses 27-34.

Clause 40. The method of clause 39 wherein the disease or disorder is an allergy, an autoimmune disease or disorder, an infection or infectious disease, or cancer.

Clause 41. The method of clause 40, wherein the infection or infectious disease is caused by a viral, bacterial or prion infection.

What is claimed is:

1. A compound of formula (I),

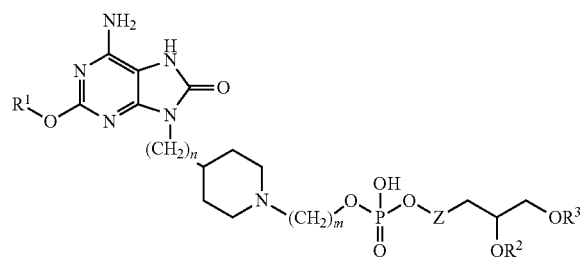

or a pharmaceutically acceptable salt thereof, wherein $R^1$ is —$CH(CH_3)(CH_2)_2CH_3$;

$R^2$ is $C(O)R^4$;

$R^3$ is $C(O)R^4$;

$R^4$, at each occurrence, is independently $C_6$-$C_{20}$ alkyl;

n is 1;

m is 2;

Z is $(C_2$ alkylene-O$)_q$; and q is 3.

2. The compound of claim 1, or a pharmaceutically acceptable salt thereof, wherein $R^4$, at each occurrence, is independently selected from the group consisting of $(CH_2)_{14}CH_3$, $(CH_2)_{10}CH_3$, $(CH_2)_{12}CH_3$, and $(CH_2)_{16}CH_3$.

3. The compound of claim 2, or a pharmaceutically acceptable salt thereof, wherein $R^4$ is $(CH_2)_{14}CH_3$.

4. The compound of claim 1, wherein the compound is a compound of formula (Ia):

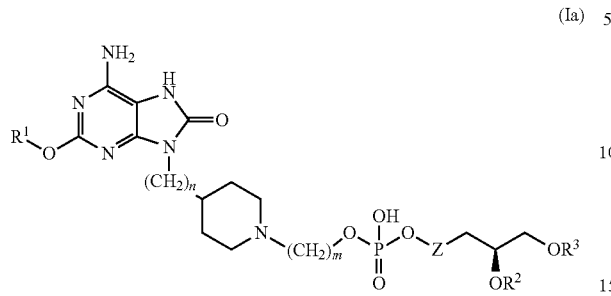

or a pharmaceutically acceptable salt thereof.

5. The compound of claim 2, wherein the compound is a compound of formula (Ia):

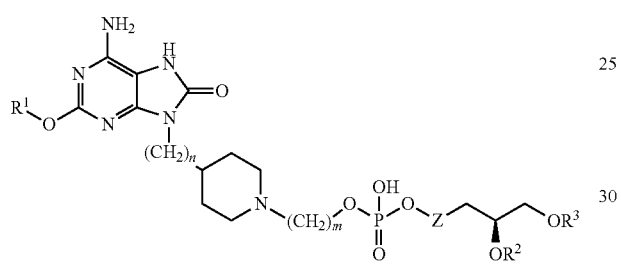

or a pharmaceutically acceptable salt thereof.

6. The compound of claim 3, wherein the compound is a compound of formula (Ia):

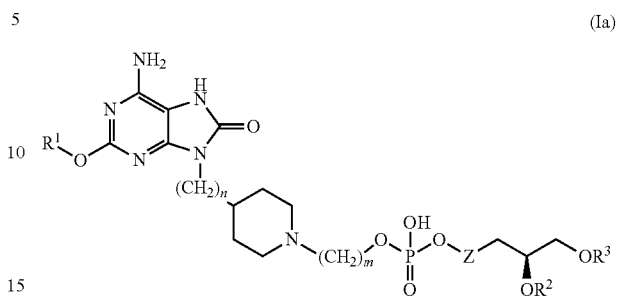

or a pharmaceutically acceptable salt thereof.

7. The compound of claim 1, or a pharmaceutically acceptable salt thereof, wherein the compound is

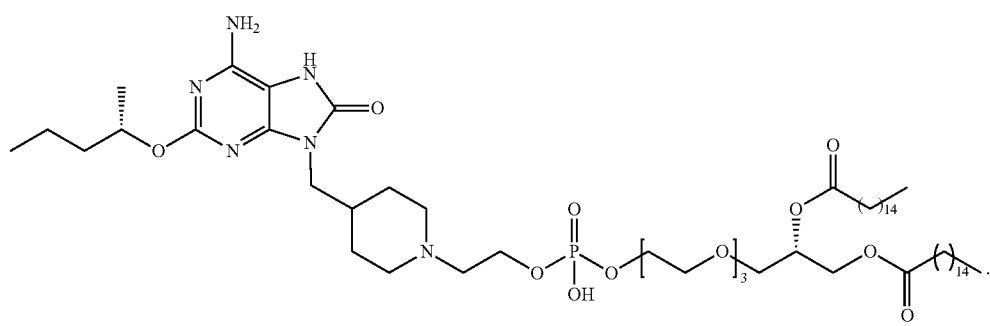

8. The compound of claim 1, or a pharmaceutically acceptable salt thereof, wherein the compound is
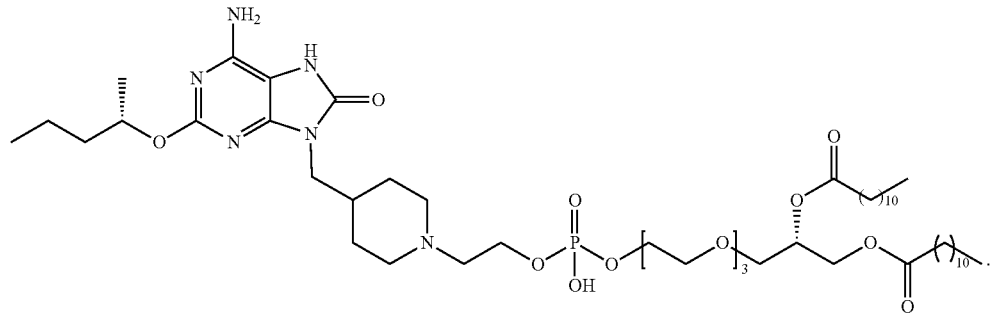
9. The compound of claim 1, or a pharmaceutically acceptable salt thereof, wherein the compound is
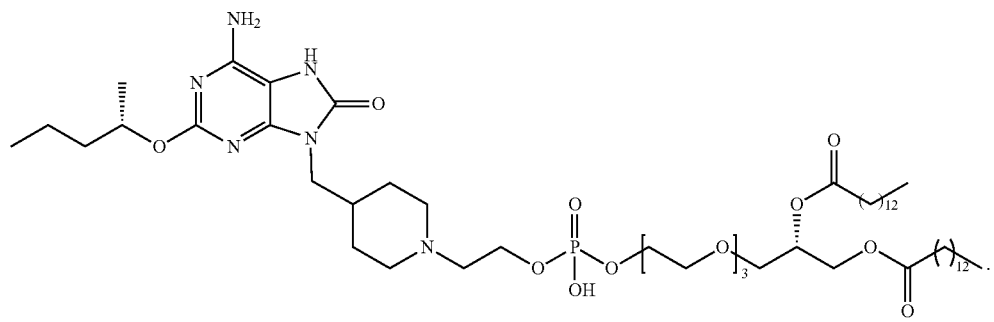
10. The compound of claim 1, or a pharmaceutically acceptable salt thereof, wherein the compound is
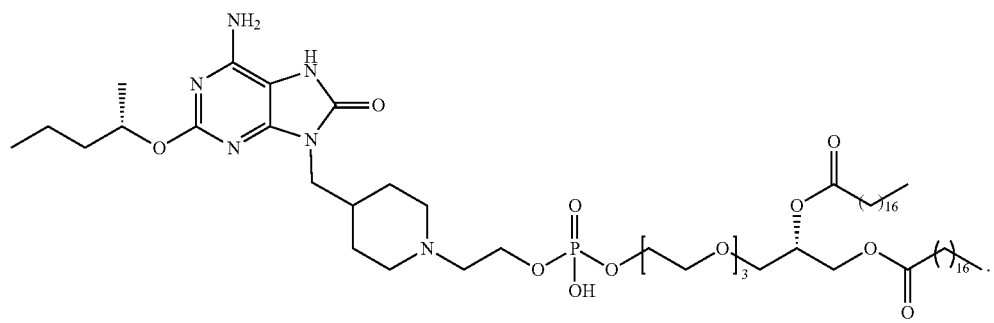
\* \* \* \* \*